US011160964B2

(12) United States Patent
Zvezdin et al.

(10) Patent No.: US 11,160,964 B2
(45) Date of Patent: Nov. 2, 2021

(54) MICRONEEDLE PATCH AND FABRICATION DEVICE FOR PRODUCTION OF MULTILAYERED MICRONEEDLES

(71) Applicant: Microneedles Inc., Wilmington, DE (US)

(72) Inventors: Vasilii Nikolaevich Zvezdin, Perm (RU); Ivan Arkadevich Kasatkin, Perm (RU); Tatiana Igorevna Akafeva, Perm (RU); Andrei Jurievich Pavlov, Naantali (FI); Iurii Alexandrovich Silov, Perm (RU)

(73) Assignee: Microneedles Inc., Wilmington, DE (US)

( * ) Notice: Subject to any disclaimer, the term of this patent is extended or adjusted under 35 U.S.C. 154(b) by 0 days.

(21) Appl. No.: 16/905,998

(22) Filed: Jun. 19, 2020

(65) Prior Publication Data

US 2020/0398035 A1 Dec. 24, 2020

Related U.S. Application Data

(60) Provisional application No. 62/864,519, filed on Jun. 21, 2019.

(51) Int. Cl.
*B29C 41/22* (2006.01)
*B29C 41/36* (2006.01)
(Continued)

(52) U.S. Cl.
CPC ......... *A61M 37/0015* (2013.01); *B29C 41/22* (2013.01); *B29C 41/36* (2013.01);
(Continued)

(58) Field of Classification Search
CPC ...... A61M 2037/0023; A61M 37/0015; A61M 2037/0053; A61M 2037/0046; A61M 2037/003; A61M 2037/0061; A61K 9/0021; B29C 39/021; B29C 39/025; B29C 39/10; B29C 41/22; B29C 41/36; B29L 2031/7544; B29L 2031/756
See application file for complete search history.

(56) References Cited

U.S. PATENT DOCUMENTS

2002/0082543 A1\* 6/2002 Park .......................... A61N 1/30
604/21
2002/0133129 A1\* 9/2002 Arias ................ A61M 37/0015
604/272
(Continued)

FOREIGN PATENT DOCUMENTS

CN 106178245 A \* 12/2016
TW 201818927 A 6/2018
WO 2018212592 A1 11/2018

OTHER PUBLICATIONS

International Search Reopor and Written Opinion PCT/US2020/038585 dated Sep. 9, 2020, 13 pages.
(Continued)

*Primary Examiner* — Quynh-Nhu H. Vu
(74) *Attorney, Agent, or Firm* — Meunier Carlin & Curfman LLC

(57) ABSTRACT

An apparatus for manufacturing a multilayer microneedle patch and a method to manufacture a multilayer microneedle patch is disclosed along with multilayer microneedle patches.

14 Claims, 19 Drawing Sheets

(51) Int. Cl.
*A61M 37/00* (2006.01)
*B29L 31/00* (2006.01)
(52) U.S. Cl.
CPC .............. *A61M 2037/0023* (2013.01); *A61M 2037/0053* (2013.01); *B29L 2031/7544* (2013.01)

(56) References Cited

U.S. PATENT DOCUMENTS

| | | | | |
|---|---|---|---|---|
| 2010/0152880 | A1* | 6/2010 | Boyden | A61K 9/0019 700/117 |
| 2014/0142541 | A1* | 5/2014 | Yan | A61K 47/38 604/506 |
| 2014/0188041 | A1* | 7/2014 | Moore | A61B 17/205 604/46 |
| 2016/0271381 | A1* | 9/2016 | Falo, Jr. | B29C 39/123 |
| 2018/0140815 | A1* | 5/2018 | Ono | A61M 37/0015 |
| 2018/0279929 | A1 | 10/2018 | Huang | |
| 2018/0304062 | A1* | 10/2018 | Falo, Jr. | A61M 37/0015 |
| 2018/0311486 | A1 | 11/2018 | Park | |
| 2018/0333898 | A1* | 11/2018 | Francis | B29C 33/40 |

OTHER PUBLICATIONS

Kim, Yeu-Chun et al.: "Microneedles for drug and vaccine delivery", Advanced Drug Delivery Reviews, Elsevier, 2012, vol. 64, pp. 1547-1568.
Prausnitz, Mark R.: "Microneedles for transdermal drug delivery", Advanced Drug Delivery Reviews, Elsevier, 2004, vol. 56, pp. 581-587.
Escobar-Chávez, Jose Juan et al.: "Microneedles: A Valuable Physical Enhancer to Increase Transdermal Drug Delivery", J Clin Pharmacol, 2011, vol. 51, pp. 964-977.
Tuan-Mahmood, Tuan-Mazlelaa et al.: "Microneedles for intradermal and transdermal drug delivery", European Journal of Pharmaceutical Sciences, Elsevier, 2013, vol. 50, Issue 5, pp. 623-637.
Kim Miroo et al.: "The Troy Microneedle: A Rapidly Separating, Dissolving Microneedle Formed by Cyclic Contact and Drying on the Pillar (CCDP)", Plos One, 2015, pp. 1-14.
Crichton, Michael L. et al.: "The viscoelastic, hyperelastic and scale dependent behaviour of freshly excised individual skin layers", Biomaterials, Elsevier, 2011, vol. 32, pp. 4670-4681.
Davis, Shawn P. et al.: "Insertion of microneedles into skin: measurement and prediction of insertion force and needle fracture force", Journal of Biomechanics, Elsevier, 2004, vol. 37, pp. 1155-1163.
Gomaa, Yasmine A. et al.: "Effects of microneedle length, density, insertion time and multiple applications on human skin barrier functions: Assessments by transepidermal water loss", Toxicology in Vitro, Elsevier, 2010, vol. 24, pp. 1971-1978.
Larrañeta, Eneko et al.: "Microneedle arrays as transdermal and intradermal drug delivery systems: Materials science, manufacture and commercial development", Materials Science and Engineering R, Elsevier, 2016, vol. 104, pp. 1-32.
Fukushima, Keizo et al.: "Two-Layered Dissolving Microneedles for Percutaneous Delivery of Peptide/Protein Drugs in Rats", Pharm Res, Springer, 2011, vol. 28, pp. 7-21.
Sasseville, Denis et al.: "Allergic Contact Dermatitis From Hydrocolloid Dressings", American Journal of Contact Dermatitis, 1997, vol. 8, No. 4, pp. 236-238.
Chu, Leonard Y. et al.: "Fabrication of Dissolving Polymer Microneedles for Controlled Drug Encapsulation and Delivery: Bubble and Pedestal Microneedle Design", Journal of Pharmaceutical Sciences, 2010, vol. 99, No. 10, pp. 4228-4238.
Wang, Min et al.: "Recent advances in the design of polymeric microneedles for transdermal drug delivery and biosensing", Lab on a Chip, Royal Society of Chemistry, 2017, vol. 17, pp. 1373-1387.
Wang, Qi Lei et al.: "A fabrication method of microneedle molds with controlled microstructures", Materials Science and Engineering C, Elsevier, 2016, Vo. 65, pp. 135-142.
Demir, Yusuf K. et al.: "Characterization of Polymeric Microneedle Arrays for Transdermal Drug Delivery", Plos One, 2013, vol. 8, Issue 10, pp. 1-9.
Larrañeta, Eneko et al.: "Microwave-Assisted Preparation of Hydrogel-Forming Microneedle Arrays for Transdermal Drug Delivery Applications", Macromolecular Materials and Engineering, 2015, vol. 300, pp. 586-595.
Lee, Jeong W. et al.: "Dissolving microneedles for transdermal drug delivery", Biomaterials, Elsevier, 2008, vol. 29, pp. 2113-2124.
Lutton, Rebecca E. M. et al.: "Microneedle characterisation: the need for universal acceptance criteria and GMP specifications when moving towards commercialisation", Drug Deilv. and Transl. Res., Springer, 2015, vol. 5, pp. 313-331.

\* cited by examiner

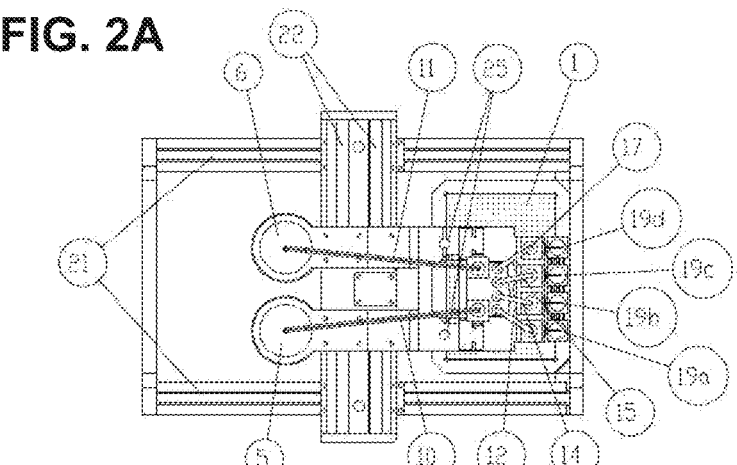
FIG. 2A
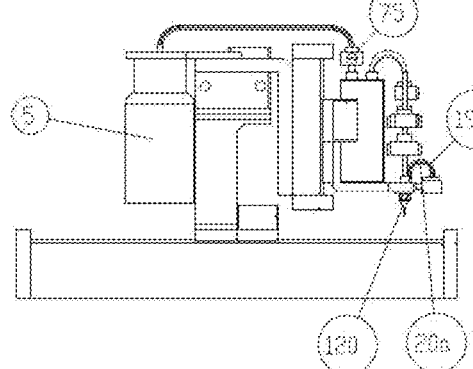
FIG. 2B
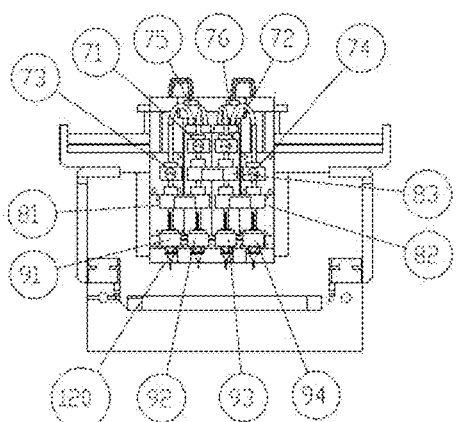
FIG. 2C
FIG. 2

FIG. 3A
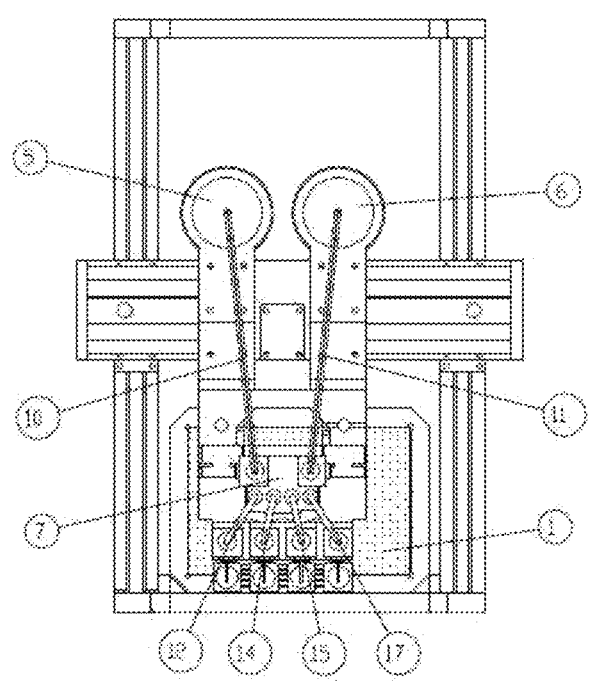
FIG. 3B
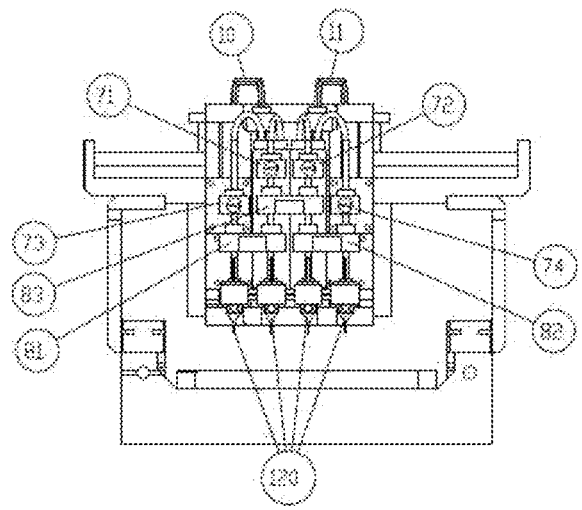
FIG. 3

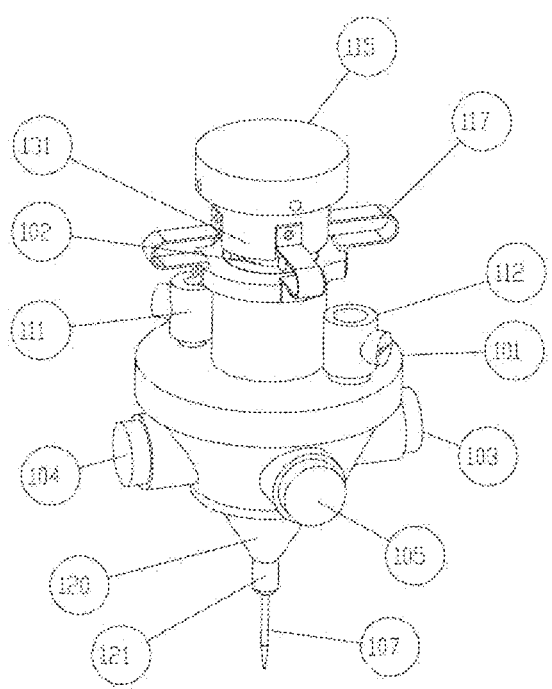 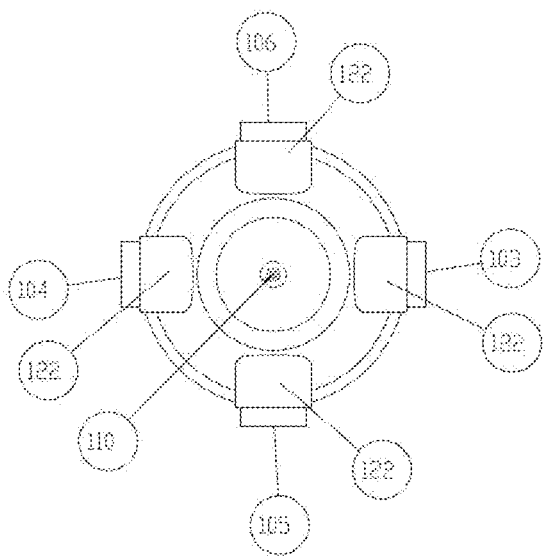
FIG. 4A  FIG. 4B
FIG. 4

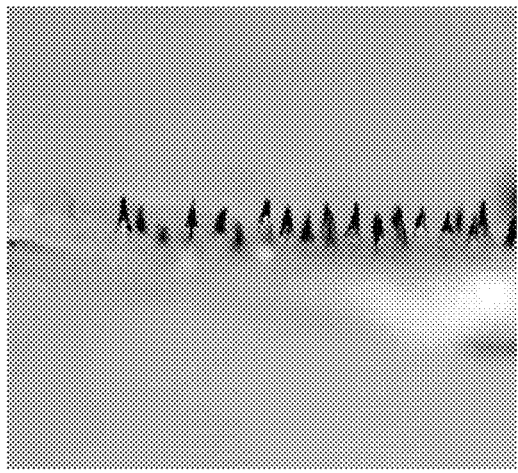
FIG. 16A
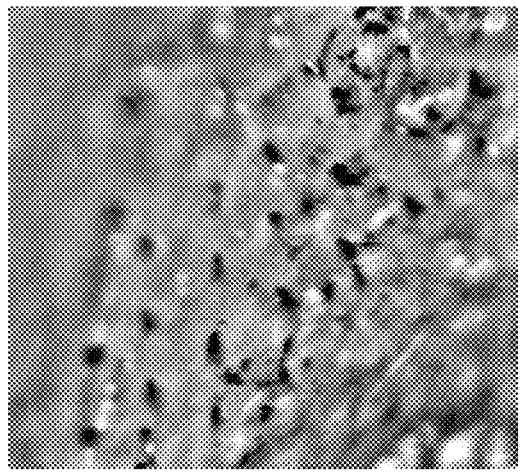
FIG. 16B
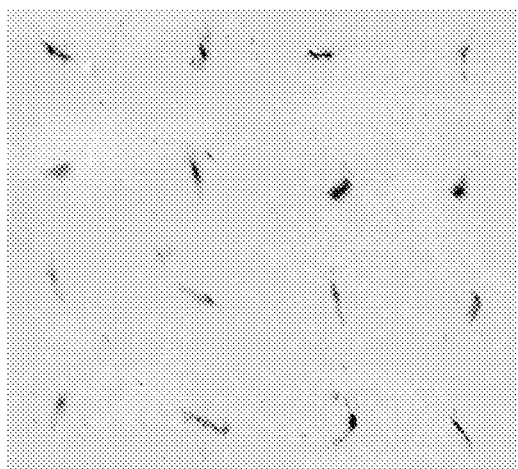
FIG. 16C
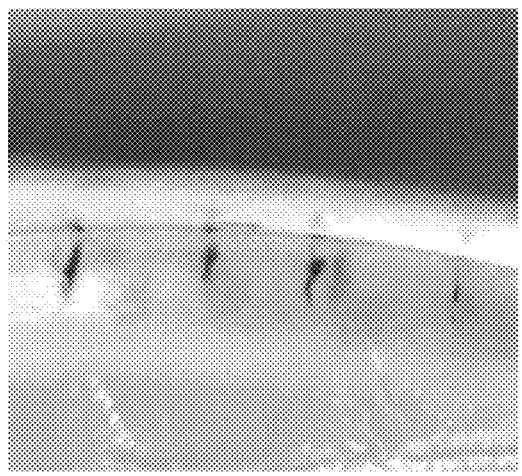
FIG. 16D
FIG. 16

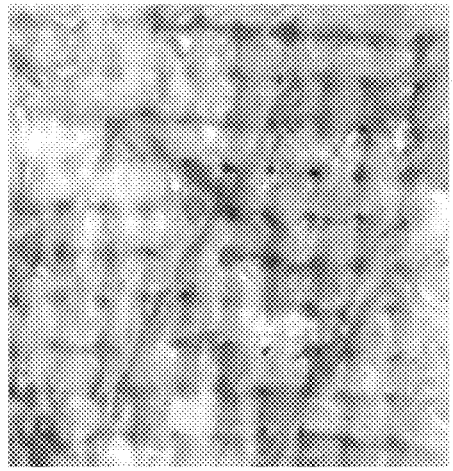 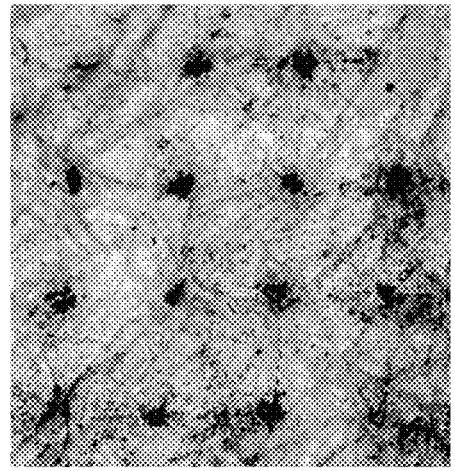
FIG. 17A　　　　　　FIG. 17B
FIG. 17

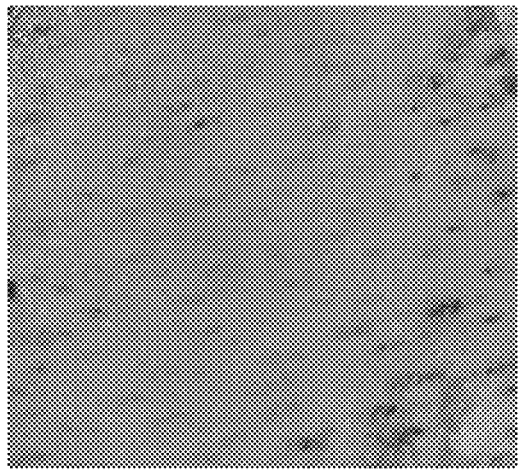
FIG. 18A
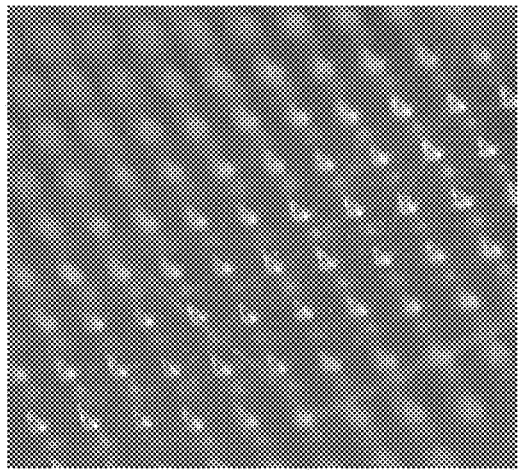
FIG. 18B
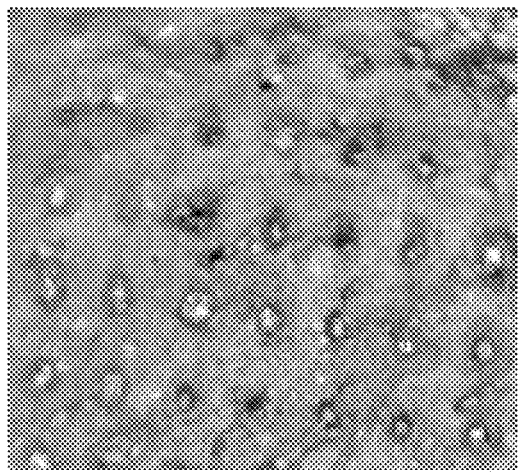
FIG. 18C
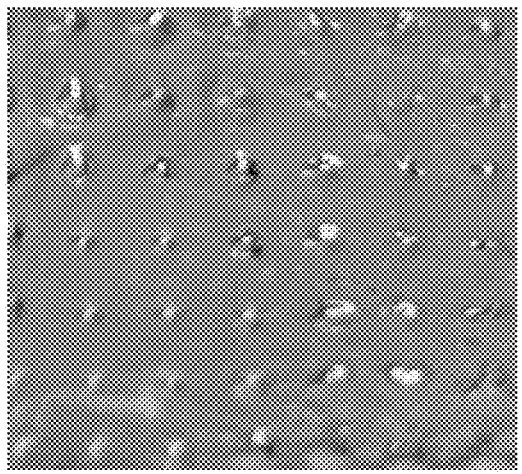
FIG. 18D
FIG. 18

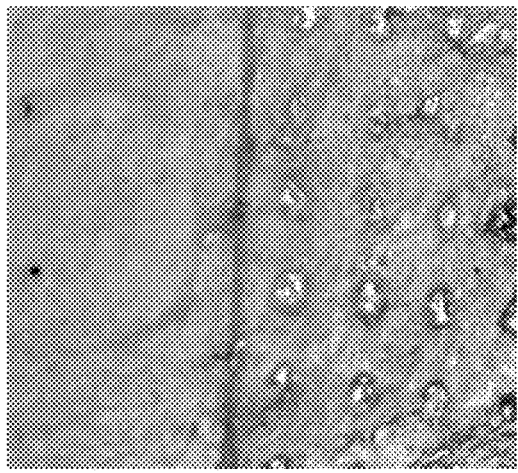
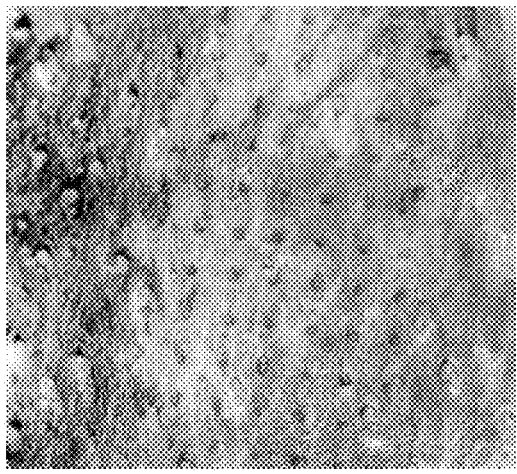
FIG. 19A  FIG. 19B
FIG. 19

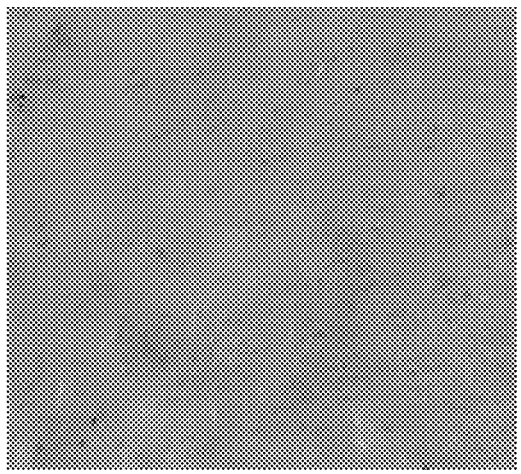
FIG. 20A
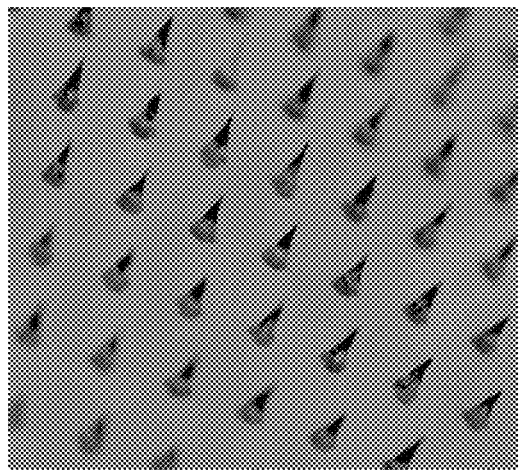
FIG. 20B
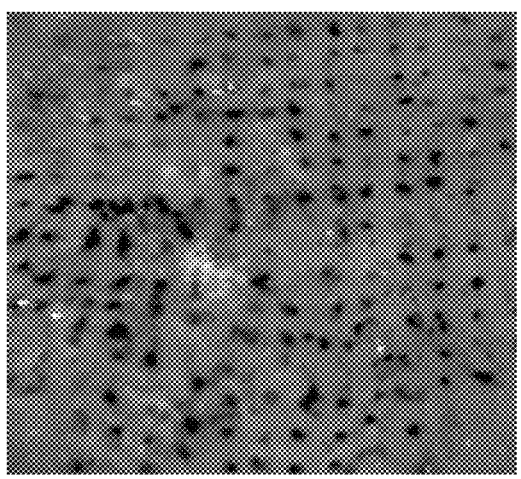
FIG. 20C
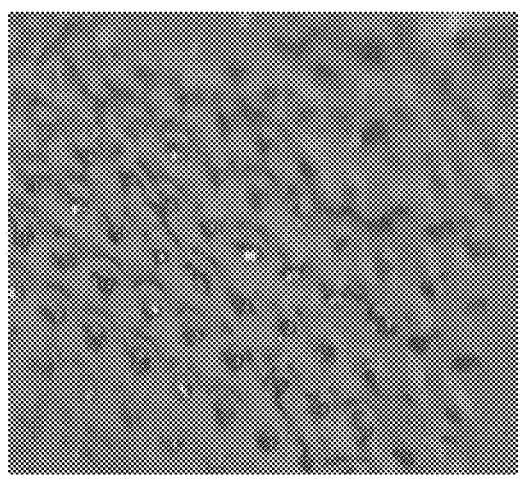
FIG. 20D
FIG. 20

MICRONEEDLE PATCH AND FABRICATION DEVICE FOR PRODUCTION OF MULTILAYERED MICRONEEDLES

PRIORITY

This application claims priority of U.S. Provisional patent application No. 62/864,519 filed on Jun. 21, 2019, the content of which is incorporated herein by reference in its entirety.

FIELD OF THE INVENTION

The present disclosure belongs to microneedle (MN) technology for medical applications and particularly to drug delivery into the skin using soluble microneedle patches. Depending on the composition of active components, the purpose of injection may vary from medical vaccination to cosmetic purposes. This invention discloses a microneedle (MN) array comprising multilayer dissolving detachable microneedles (DDMN) fabricated by sequential precision layer-by-layer biopolymer aqueous solution deposition. This enables rapid detachment of the MN tips from DDMN base after attachment of the MN patch to the skin. The released microneedles remain in the skin for further drug release.

BACKGROUND OF THE INVENTION

Microneedle (MN) technology offers an efficient and minimally invasive drug delivery method compared to conventional transdermal patches and intravenous injections. MNs breach the stratum corneum painlessly, improve the permeability of the skin and enhance transdermal drug delivery. Biodegradable MNs have been actively studied recently. The advantage of this type of MNs is extended drug release. The MNs are composed of biodegradable materials that have higher drug payloads with no potential biohazardous waste after application to the skin. Most existing biodegradable MNs are made of water-soluble polymers that dissolve and release drug molecules after contact with interstitial fluid in the skin. However, the polymers of these MNs have drawbacks in terms of mechanical strength and stability.

Traditional MNs are usually fabricated on sticky flat patches that facilitate their insertion into the skin. These patches are attached on the skin surface until they are completely dissolved. Due to the viscoelastic properties of skin, however, MNs on a flat patch often do not completely penetrate into the skin, even with a strong enough insertion force, thus complicating delivery of the full amount of encapsulated drugs. Patch-based MNs must be attached on skin for a relatively long time to allow full dissolution of the polymer matrix to the skin, which may generate an allergic response in some patients. Furthermore, additional devices used for inserting soluble microneedle applicators can be inconvenient for the end user, especially in cases when prolonged exposure is necessary. For these reasons, a better MN delivery system with complete insertion and rapid administration is needed.

Several approaches have been suggested to overcome the limitations of traditional MN patches. Two-layered MNs with encapsulated drugs only at the tip have been introduced to overcome incomplete drug delivery [Fukushima K. et al. 2011, Pharm. Res. 28, 7-21]. Even with incomplete MN insertion, this two-layered system can deliver all encapsulated drugs without a loss.

Alternatively, a system where MNs are attached to a water-soluble backing film has been developed to deliver the MNs by dissolving the water-soluble film [Fukushima et al. 2011. Pharm. Res. 28, 7-21]. In this system, water is used as a dissolving accelerator, allowing drugs in the MNs to be delivered rapidly (within 10 min). However, this MN formation also depends on a flat backing film, and, therefore, complete insertion is needed. In addition, the water used to dissolve the patch may also dissolve the portion of the MNs not completely inserted into the skin. On the other hand, if a polymer containing the active substance is dissolved very quickly, then allergic reactions can occur [Sasseville D. et al 1997 Dermatitis 8, 236-238]. In some cases, however, adding water as dissolving accelerator may not be beneficial or desired, especially when the procedure precisely demands a slow release of the active substance (hormonal drugs).

There is a method of obtaining microneedles using molds with through holes, in which one section is larger than the other forming mirconeedles with a conic shape (TW201818927). To make a needle, one of the ends of the hole is closed with a gas-permeable membrane with a pore diameter of 25 to 450 nm, a polymer is applied from the other end (weight from 40 to 360 kDa) and then the composition is sucked through the hole. Depending on the molecular weight of the polymer, the range of input concentrations of the latter ranges from 45 to 60 vol. % up to 13-22 vol. %. However, this method is difficult to use for manufacturing multilayered structures.

US2018279929 describes a method for producing a microneedle device including conductive materials and electronic components. In this case the microneedle device is an array of microneedles made of insoluble materials. It is known that methods for obtaining insoluble microneedles usually imply a physical effect on a material characterized by high values of the energy transferred to the material being processed (for example, melting, plasma etching, laser ablation, photolithography, chemical or physical deposition from the gas phase, etc.). This in turn, makes the above-mentioned group of methods inappropriate for obtaining microneedles containing a biologically active substance, since these substances lose their biological activity under high-energy effects.

Even though the method described in US2018279929 allows resulting insoluble microneedles to be covered with a layer of biosoluble polymer containing the active substance to reduce skin allergization when introducing a microneedle device, this approach only allows active substance on the surface of the microneedles. When introducing needles with an active substance sprayed on them into the skin, it is difficult to control the real dose of the injected substance, therefore this approach cannot provide precision dosing.

US2018311486A1 describes a method for continuous (aspiring to industrial) method for producing hyaluronic micro-needle patches. The installation for the production of microneedle products is represented by a set of rollers rolling a film that performs the function of the backing of the micro needle applicators. In addition to the rolling function, a series of rollers applies the necessary components to the film being rolled: for example, the first complex of rollers applies an adhesive layer to a clean film, the second complex of rollers takes a solution of hyaluronic acid from the drain tank and forms microneedles directly on the adhesive layer as the surface of the roller supplying the hyaluronic acid solution is speckled with cone-shaped holes. At the last stage, a film with molded and dried microneedles is collected and sent to further production stages. By duplicating and combining sets of rollers, it is theoretically possible to produce single-layer microneedles connected to each other by a common base layer of the polymer from which the needles themselves are made.

However, the above described method, due to its specificity, does not allow obtaining microneedles, the structure of which is represented by several horizontal layers. This method, probably, can be used to make single-layer microneedles containing a layer of bio-soluble polymer between the needle base and the film backing. However with this approach it will not be possible to achieve rapid separation microneedle layer, since the polymer layer between the microneedle base and the film backing during application of the applicator will be in an environment that is relatively poor in moisture for the layers to separate.

Production of hyaluron microneedle patches using rolling rollers, on the surface of which there are cavities for the formation of microneedles is also disclosed in US2018311486A1. According to the publication, the process is fast and continuous. The method is interesting as an industrial approach to production, it can also be used to hypothetically make disconnecting needles. However, the disconnecting layer could only be between the base of the needle and the backing adhesive.

WO2018212592 claims a recipe for bio-soluble needles made of hyaluronic acid (HA) containing a specific active substance: donepezil. It is indicated that the needles contain up to 43% of donepezil of the total weight of the needle. The used HA is ranked by weight from 300 to 800 kDa, the characteristic viscosity of the composition is in the range from 0.15 to 0.25 $m^3$/kg. The strength of the needle is from 0.058 N to 0.1 N. The length of the needle is 580-900 microns, the tip diameter is from 35 to 110 microns. Among the declared effects that highlight this invention are the high mechanical strength of the needle, and the possibility of introducing relatively high concentrations (up to 43%) of the active substance. Also, it is stated that during the study of solubility it was possible to determine the time of complete dissolution of the needles to be ~2 hours. The published application also specifies a method for obtaining needles, namely: blowing air through a meniscus separating a drop drawn out by two surfaces. Thus, the above publication discloses a set of options for microneedle formulations for the delivery of a specific drug. However, the publication does not teach multilayer biosoluble microneedles or methods to make them.

There is a need for a method to make dissolving detachable microneedles to improve the currently known technologies and to provide microneedles the tip of which can rapidly detach from the multilayer base after a microneedle patch is attached to the skin.

These problems can be solved by dissolving detachable microneedles (DDMN) technology of this disclosure. This technology can reduce time of the procedure with no need to enhance the dissolution rate of the microneedle tips (microcapsules) containing active substances.

SUMMARY OF THE INVENTION

This invention provides a method in which with the help of precision layer-by-layer deposition of solutions in the wells of dimethylpolysilixane (PDMS)-mold (Mold) and layer-by-layer drying and/or polymerization of the solution, one can create multi-layer microneedles with quick-dissolving middle layer and active substance contained only in one layer (tip needles). This precision dosing technology allows creation of this type of microneedles thanks to adaptive injection heads of the fabrication device, dosing accuracy and lack of waste (there is no need to wash off one polymer layer in order to apply another one).

The disclosed method of precision layer dosing allows making microneedles with the following properties:
1. Removable microneedle patch, when the back of the patch can be removed after 15-25 minutes of its application to the skin and the remaining needle tips continue dissolve in the dermis within no more than 24 hours;
2. Microneedles for creation a "depot" in the tissue, when the back is removed after 15-25 minutes, and the needle tip is a "capsule" from which the active substance is released within a few days or weeks.

Thus, microneedles created by the technology disclosed here are potentially capable of introducing a "capsule" with the active substance to the level of the papillary and reticular layers of the dermis, while the residence time of the applicator (back of the patch) on the skin is reduced to 15-25 minutes due to rapid dissolution of the middle layer that connects the microneedle tips and backing of the patch. Reduction of the application time enables maximum introduction of active components without the use of specialized devices to ensure uniform long-term pressure on the patch.

The present invention provides a microneedle patch and a fabrication device. The microneedle patch contains a matrix of soluble microneedles. The microneedles are made of multiple components, each of the components has its specific function. The microneedle comprises multiple layers, preferably three layers: a first layer being a sharp end for effective painless penetration into the skin, a middle layer comprising first active component, and the third layer comprising second active component. The third layer of the microneedles or the microneedle matrix is connected to a top base layer of the patch. A complex structure of the microneedle is used for most efficient drug administration into the skin and at the same time providing skin treatment. The microneedles of this invention may effectively be used for cosmetic purposes when the penetration depth is about 300 µm. The composition of the microneedles is based on polymeric solutions, medicine/drug and active components.

In order to make the sterile multilayered microneedles, a new fabrication device and an adaptive injection nozzle were designed. The fabrication device comprises a system of tanks, transition lines, electro-mechanical mechanisms for moving the injection heads over the mold in three directions, electronics devices to control the fabrication process and a software computer program for automatic control of the devices.

The fabrication device provides preparation of the liquid polymeric components and delivery of the components into the injection head. The adaptive injection nozzle is a device containing a microchamber (also called an inner cavity) filled with the liquid polymeric solution, a microtube for transferring the polymeric solution with added medicine and/or active components into the microcavities of the mold.

Because the micro-dosed droplets have to have an exact mass, the adaptive injection heads are equipped with pulsed micro-pumps that produce increase of pressure in the microchamber (inner cavity). The pressure inside the liquid is used to move the liquid solutions along the microtube and delivering the precise amount of the material into the cavity of the mold. The pressure is correlated with the mass of the fraction of the material to be dropped into the microcavity of the mold.

The process uses a feedback between the micro-pump power and the mass of the material inside the chamber. After the material of the first layer is filled in all microcavities of the mold, the layer is dried until total solidification followed by next fabrication steps. The polymeric technology allows integration of the microneedle matrix on flexible substrates. Therefore, the application of the microneedle patches to the human skin is easy and painless.

It is an object of this invention to provide an apparatus for manufacturing a multilayer microneedle patch, comprising: a mold having a plurality of microcavities; one or more containers for liquid chemical materials and active components; an injection assembly connected with the one or more containers, the injection assembly comprising at least one adaptive injection device comprising a nozzle having an inner cavity and at least two inlets to fill the inner cavity with the liquid chemical materials, a piston for adjustment of volume and pressure in the inner cavity, and a microtube for injection of the chemical material to the microcavities; and a positioning mechanism configured to provide a precise movement of the injection assembly along three perpendicular axes above the mold.

According to certain embodiments the microcavities of the mold have conical shape, and the mold is oriented in the horizontal plane, and the nozzle of the injection assembly is oriented perpendicularly to the upper surface of the mold facing the microcavities.

According to certain embodiments the apparatus comprises a dosing system comprising mixers for mixing liquid chemical materials with active components and transferring the mixture to the injection assembly.

According to certain embodiments the dosing system is configured to prepare liquid chemical materials composed of polymers to polymeric solutions for a multilayer structure of the microneedles.

According to certain embodiments the apparatus comprises at least one mixer combined into a first stage mixer and connected to a transmission line in between the dosing system and the at least one container enabling preparation of base polymeric components before transferring them into the dosing system or directly to the injection assembly.

According to some embodiments at least one transmission line of the first stage mixers is connected directly to the injection assembly avoiding the dosing system when no further mixing of materials is needed.

According to certain embodiments the injection assembly comprises at least one additional piston for adjustment of the volume of the polymeric solution in the inner cavity.

According to some embodiments n the microtubes of at least one injection device have inner diameter small enough to create capillary forces of the polymeric solution inside the microtube to resist polymer flow through the microtube and prevent the flow when the internal pressure of the polymeric solution inside the inner cavity is less than a specific flow pressure.

According to certain embodiments at least one additional piston provides fast compression of the polymeric component inside the inner cavity increasing the inner pressure above the specific flow pressure within 1 to 500 ms, enabling injection of the polymeric component from the inner cavity through the microtube into the microcavity of the mold, the volume of the injected droplet being defined by difference between two opposite forces, one of which is defined by pressure of the polymeric component inside the inner cavity multiplied by the microtube's cross-sectional area and the other integrated force is determined by capillary forces inside the microtube, providing self-switching off the injection process when the opposite forces compensate each other.

According to certain embodiments the microtube is supplied with an ultrasonic vibrator that enables micro-vibrations of the microtube of the injection nozzle reducing the capillary forces enabling transferring polymeric solutions having different viscosities.

According to certain embodiments the frequency of the ultrasonic vibrator ranges from 1 KHz to 5 MHz and correlated with viscosity of the liquid material.

According to certain embodiments nozzle is supplied with an ultrasonic vibrator enabling micro-vibrations of the polymeric material inside the inner cavity to make the polymeric material more homogenous and improving its flow through the nozzle.

According to certain embodiments at least one additional piston for volume regulation is connected to an external pressing mechanism that provides an external force to the piston for compensation of the internal pressure of the polymeric component in the inner cavity acting on the inner surface of the piston.

It is another object of the invention to provide a method of manufacturing multilayer soluble microneedles and packaging them into a flexible patch for further use for transdermal injections of active bio-chemicals into the skin comprising: a) providing a mold having a plurality of conical microcavities; b) preparing sequentially at least three layers of different polymeric solutions forming the multilayers of the microneedles; c) filling the conical microcavities of the with polymeric solutions starting from a tip of the microneedle structure, followed by deposition of at least one intermediate/middle layer, followed by deposition of at least one base layer; d) vacuuming and drying each layer after the deposition step; e) depositing of a superficial cover base layer forming a top patch structure by covering the top surface of the mold with a film providing strong mechanical connection of all microneedles to the cover base layer and formation of a flexible patch; e) vacuuming and drying the cover base layer; f) preparing adhesive and protection layers on top of the cover base layer; and g) removing of the flexible patch from the mold.

According to certain embodiments the polymeric solution for the first layer forming a tip of a microneedle is prepared to comprise a hard polymeric solution with active components, and the polymeric solution for the second intermediate layer is prepared to comprise a soluble polymeric solution that dissolves faster in the skin than other layers of the needle patch.

According to some embodiments the base layer is manufactured to contain another active component for treatment of the top surface of the skin.

According to some embodiments the polymeric composition forming the first layer is prepared to include a drug-polymer composition, the polymeric composition forming the second layer is prepared to consist of a quick-dissolving polymer, and the polymeric composition forming the third layer is manufactured to form a back-layer and also configured to partially penetrate into the microcavities if the mold to form pedestals-like structures of the microneedles.

According to some embodiments additional functional layers are formed in between two neighboring structural layers by inter-diffusion of the chemical components into a depletion layer at the interface between the deposited layers.

It is a further object of this invention to provide a multilayer soluble microneedle patch comprising a multitude of microneedles having at least three layers, the first layer being tips of the microneedles and comprising a hard polymer and active components, the second layer being a fast dissolving polymeric layer, and the third layer being a base layer.

DESCRIPTION OF DRAWINGS

FIG. 2, composed of FIG. 2A, FIG. 2B, and FIG. 2C, shows detailed pictures of the fabrication device. FIG. 2A is a top view of the device, FIG. 2B is a side view of the device, and FIG. 2C is a front view of the device. In these figures the following elements are shown: the mold 1, rods 21, 22, 25, containers 5, 6, transmission lines 10, 11, tubes 12, 14, 15, 17, transmission lines 19a-d, 20a, pumps with valves 71, 72, 73, 74, 75, 76, mixers, 81, 82, 83, mixers with pumps 91, 92, 93, 94, injection nozzle 120.

FIG. 3, composed of FIG. 3A and FIG. 3B, shows detailed pictures of the fabrication device. FIG. 3A is a top view of the device, FIG. 3B is a front view of the device. In these figures the following elements are shown: the mold 1, containers 5,6 distribution device 7, transmission lines 10, 11, tubes, 12, 14, 15, 17, injection nozzles 120, pumps with valves 71, 72, 73, 74, mixers 81, 82, 83.

FIG. 4, composed of FIG. 4A and FIG. 4B, shows an adaptive injection device. FIG. 4A is the adaptive injection device shown from the side, and FIG. 4B is the same adaptive injection device shown from the bottom. In these figures the following elements are shown: force-control mechanism 131, piston 102, flange 115, fixation springs 117, nozzle 120, flange 101, vibrator 121, tubes 122, pistons 103, 104, 105, ultrasonic vibration device 106, microtube 107 with end 110, pump with valve 111, pump with valve 112.

In FIG. 5B, a section going through inlets 108, 109 is shown. The following elements are shown in these figures: cavity 100, pressing mechanism with force-control 131 comprising a piston 102 with rods 118, a flange 115 with holes 132 and 116, fixation springs 117, nozzle 120 with vibrator 121 and cavity 100, tubes 122, pistons 103, 104, microtube 107, smaller inlet 108, bigger inlet 109, pumps with valves 111, 112, flange 101 with hole 135.

FIG. 16 is composed of FIG. 16A, FIG. 16B, FIG. 16C, and FIG. 16D, which respectively show: A) Type 1 DDMN loaded with 0.05% black iron oxide pigment before insertion test; B) Type 1 DDMN loaded with 0.05% black iron oxide pigment after insertion test; C) Agarose gel sample pierced by DDMN sample loaded with 0.05% black iron oxide pigment (top view); D) Agarose gel sample pierced by DDMN sample loaded with 0.05% black iron oxide pigment (perpendicular slice).

FIG. 17 is composed of FIG. 17A and FIG. 17B, which are photographs of human cadaver skin samples penetrated by DDMNs. FIG. 17B shows an undyed sample, whereas FIG. 17B shows a sample dyed with methylene blue.

FIG. 18 is composed of FIG. 18A, FIG. 18B, FIG. 18C, and FIG. 18D, which are photographs of porcine cadaver skin samples and DDMN test samples. FIG. 18A is a porcine cadaver skin sample surface morphology before DDMN application; FIG. 18B shows a DDMN test sample before insertion into skin sample; FIG. 18C is a porcine cadaver skin sample surface morphology after DDMN application; FIG. 18D shows a DDMN test sample after insertion into skin sample.

FIG. 19 is composed of FIG. 19A and FIG. 19B, which are photographs of porcine cadaver skin samples. FIG. 19A is a pierced porcine cadaver skin morphology at the interface between untouched (left from the interface) and pierced skin sites (right form the interface); FIG. 19B is a pierced porcine cadaver skin sample dyed with 1% aqueous methylene blue solution.

FIG. 20 is composed of FIG. 20A, FIG. 20B, FIG. 20C, and FIG. 20D, which are photographs of porcine cadaver skin samples and DDMN test samples. FIG. 20A shows a porcine cadaver skin sample surface morphology before Type 1 DDMN application; FIG. 20B shows a Type 1 DDMN test sample before insertion into skin sample; FIG. 20C shows a porcine cadaver skin sample surface morphology after DDMN application; FIG. 20D shows a Type 1 DDMN test sample after insertion into skin sample.

DETAILED DESCRIPTION OF THE INVENTION

Figure 1:
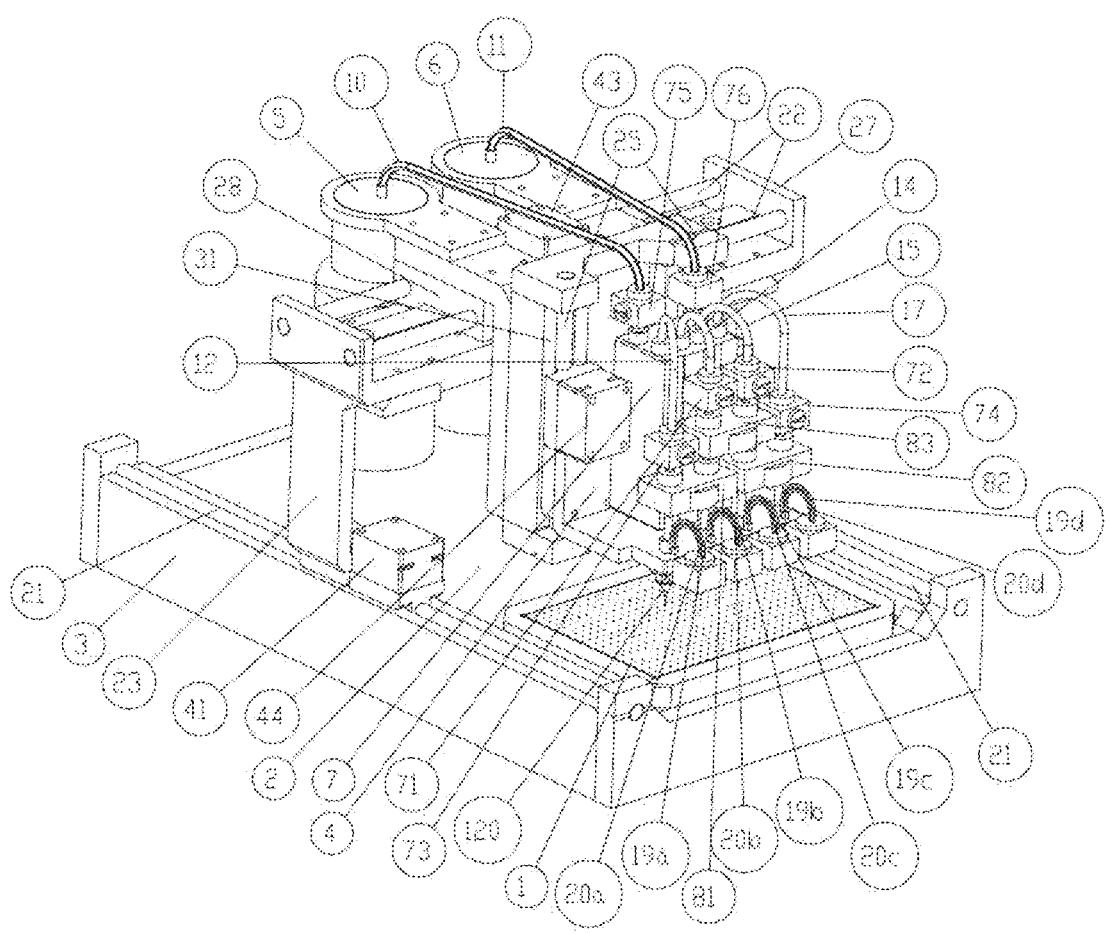
FIG. 1. A fabrication device for manufacturing multi-layer microneedles by precision dosing of polymer solutions. In the figure, the following elements are shown the mold 1, base 2, horizontal sliding mechanism in x-direction 3, slider x-direction 23, motor x-direction 41, rods 21, horizontal sliding mechanism y-direction 27, rods 22, slider y-direction 28, motor y-direction 43, vertical sliding mechanism z-direction 31, rods 25, slider z-direction 4, motor z-direction 44, tanks of liquid/polymeric materials 5, 6, transmission lines 10, 11, pumps with valves 75, 76, mixer 7, tubes 12, 14, 15, 17, pumps with valves 71, 72, 73, 74, mixers 81, 82, 83, injection nozzle 120, transition lines 19a-d, 20a-d.

The method disclosed here enables creating reproducible multilayer, preferably 3-layer microneedles satisfying all the basic requirements for the strength and penetration ability of microneedles. Precision layer-by-layer dosing of polymers allows to create 3-layer and, also, multi-layer modifications of microneedles, which expands the functionality of microneedle applicator. These microneedle applicators allow to reduce the time of application (when using the average quick-dissolving layer in the needle) and/or to inject several drugs or active agents without mixing them (mixing 2 or more drugs in one polymer solution often negatively affects their activity).

Precision layer-by-layer technology can be used to create cosmetic microneedle applicators, as well as applicators for the delivery of drugs and vaccines. For example, most of the existing products on the cosmetology market are made of hyaluronic acid with medium molecular weight (400-500 kDa) and are characterized by overnight processing (the recommended procedure time is 2 to 6 hours). The method disclosed here allows to reduce the time of the cosmetic procedure with the application of microneedles to about 25 minutes. After removal of the applicator, there is a decrease in the size of the input holes from the microneedles in the stratum corneum, which minimizes the risk of infections, and the procedure does not lead to a significant violation of the integrity of the skin. The proposed technology makes it possible to create 2in1 and 3in1 solutions, when the long-dispersible high molecular weight hyaluronic acid is in the needle's tip, and a rapidly soluble low-molecular acid is in the middle layer. It is also possible to create solutions with a modified back part of the applicator, which can also dissolve and have an aesthetic effect on the skin's surface: it can reduce the negative reaction of the skin to the mechanical effect of needles by incorporating anti-inflammatory components.

One potential application of the method of manufacturing multilayer microneedles as presented here, can be injection of slowly soluble microcapsules with the help of detachable microneedle arrays to form depot of drugs (for slow release), for example, insulin, hormonal substances, etc. At the same time, the time of wearing the applicator on the skin surface can be significantly reduced for the convenience of the patient.

Also, there is a possibility of forming microneedles containing microelectromechanical (MEMS) systems, for example, by combining an array of hydrogel needles containing a "reagent" and an epoxysilane substrate containing a microchip.

It is important to recognize that the developed method of manufacturing microneedles goes beyond the scope of laboratory production and allows development of microneedles available for industrial scaling due to the use of automatized production and assessment of the quality of needles immediately after manufacture. This method allows creating microneedles with different measured parameters, various combinations of polymer layers in the needle (layer ratio), and also create applicators with different surface area.

Microneedle Patch

The microneedle patch according to this invention comprises a multilayer structure of the needles comprising a sharp tip, a middle layer containing an active component, and a third layer that comprises a second active layer. The microneedles are integrated into the matrix using a base layer. A three-layer structure is optimal for drug delivery into the skin at about 300 nm depth from the upper surface of the skin. The microneedles of this invention provide effective painless penetration thanks to the sharp profile and low height of the microneedle.

The microneedle composition is designed so that the effective dissolution times $t_1 m_1/m > t_2 m_2/m > t_3 m_3/m$, where $t_i$ is the dissolution time of 1 milligram of the material of the corresponding layer at a certain depth of the skin, $m_i$ is the mass of the material of the layer, m is the total mass of the microneedle.

This condition provides the middle layer to dissolve first in the skin and easy disconnection of the base top layer. The remining tips stay in the skin for further dissolvement. This condition is used to calculate a proper profile of the microneedle for specific active component, medical vaccine or cosmetic components, preventing overdosing. The details are described below.

Basically, the tip of the microneedle has the smallest mass and longest dissolution time, the second layer has a shortest dissolution time. After the injection, the third base layer can be relatively quickly disconnected from the microneedle patch while active components continue to dissolve until the dissolution process is completed.

Using the calculated effective dissolution times needed for efficient drug delivery into the skin, a proper microneedle geometry and fabrication process can be modelled. In accordance with the calculated geometry, a corresponding mold is produced. Then microneedle patches are fabricated using a fabrication device disclosed here.

The fabrication device provides precise positioning of the microtube 107 of the injection nozzle 120 over the mold's micro-cavities and filling them with accurate doses of the materials that include active components and mixture of the active components with base materials. This is provided by using an adaptive nozzle of the fabrication device. The adaptive nozzle provides precise amount of a polymeric solution to be injected into the mold's micro-cavities during short time intervals. This is realized by the dosing system of the device and the affective injection mechanism mounted on the injection nozzle 120 using a system of coupled piston 102 and micro-pumps, for example pulsed pistons 103, 104, 105. The piston 102 adjusts the volume of polymer in the inner cavity 100 and the initial pressure of the polymer. After the volume is adjusted, the micro-pumps 103, 104, 105 work.

The pumps used in the device vary in power and size to delivering polymeric solutions through transmission lines 10, 11 and microtubes 12, 14, 15, 17 as well as micro-pumps or syringe pumps 103, 104, 105 in the vicinity of the nozzle for injection of precise quantity of the material into the micro-cavity. The last stage is be realized when pulsed pistons 103, 104, 105, compress the polymer inside the inner cavity working individually or simultaneously in combination of two, three, four etc. depending of chemical composition of the injected material, viscosity and amount of the component per one micro-cavity.

The injection works as follows: The flange 101 of the nozzle has two inlets 108, 109—a big one 109 and a small one 108—equipped with pumps with valves 111, 112. The big inlet 109 is used for bigger volumes of the polymeric material prepared in advance and the smaller one 108 mainly for compositions of the tip layer. The pressing mechanism with force control 131 controls the volume and pressure of liquid in the micro-tank 100 by moving a piston 102 inwards or outwards and down to increase or decrease the volume of the inner cavity 100. When the pumps valves 111, 112 are closed, the piston 102 compresses the liquid inside the inner cavity 100. The pressing mechanism with force control 131 comprises a piston 102 that is balanced from one side by the pressure of liquid in the microtank (inner cavity) 100, acting on the bottom side of the piston and from the other side by external opposite force acting on the top surface of the piston. The pressure of the liquid inside the microtank (inner cavity) 100 is limited by the capillarity force inside the injector microtube 107. When the pressure of the liquid is higher than the capillarity force, the liquid moves through the microtube 107 and drops outside onto the mold. The pressing mechanism with force-control 131 is equipped, for example, with a piston 102 having cylindrical rods 118 that can move along holes 132 in the flange 115. The holes 132 are connected through side holes 116 to an external tank with pressurized air or liquid. When the external air/liquid pressure increases/decreases, the piston 102 moves down/up. This balance is reached at pressure equilibrium between the liquid in the microtank (i.e. inner cavity) 100 and the capillary force in the microtube 107. The pressing mechanism with force-control 131 is fixed on the flange 101 with springs 117. The flange 101 has a cylindrical hole 135 for placement of the piston 102. When the nozzle 120 is positioned over the micro-cavity of the mold, one or more of the pulsed pistons, 103, 104, 105, provide pressure increase of the liquid in the microtank (inner cavity) 100 through tubes 122 connected to the nozzle. The nozzle 120 can be equipped with an ultrasonic vibrator 106 that is used for making the polymeric component inside the cavity 100 more homogenous enhancing its flow through the nozzle. As the inner pressure of the liquid increases, the material starts to flow through the micro-tube 107 and drop into the micro-cavity. This reduces the inner pressure of the liquid and the system returns to the balance after a certain mass of the material is removed. This mechanism allows injection of the precise mass of the components into the micro-cavity in accordance with a recipe.

Fabrication Device

The fabrication device is shown in FIGS. 1-5. It comprises the mold 1 mounted on the base; positioning mechanism that provides precise movement along 3 axes using horizontal sliding rods 21, 22 and vertical sliding rods 25; containers 5, 6 for injected materials, main transition lines consisting of tubes 10, 11; valves 75, 76 connected to the main distribution device (also called mixer) 7 mounted in the vertical sliding mechanism 4; distribution transition lines consisting of tubes 12, 14, 15, 17, pumps with valves 71, 72, 73, 74 connected to the distribution lines; mixers 81, 82, 83 for first type of materials; mixers with pumps 91, 92, 93, 94 for second type of materials; exchange transition lines 19a, 19b, 19c, 19d connected the mixers 91, 92, 93, 94; transmission lines 20a, 20b, 20c, 20d, for second type of materials, injection nozzles 120, electronic devices to control positioning mechanisms, pumps, sensors and injection heads, high-torque stepper motor controllers for precision positioning of the needles above the micro-cavities; syringe pump 103; ultrathin dispensing needles 107 with an inner diameter of 35 to 70 microns, preferably 40-60 microns, most preferably about 50 microns; "machine vision" type sensors that additionally correct the positioning of the needle just above the micro-cavity and "lowering" the needle into at 200-300 microns. The microtubes/dispensing needles 107 can be supplied with a vibrator 121, for example a piezoelectric ring, that enables micro-vibrations of the microtube of the injection nozzle reducing the capillary forces enabling transferring polymeric solutions having different viscosities.

The distribution device 7 provides flow of polymeric materials from tanks 5, 6 into transmission lines 12, 14, 15, 17 so that the two components can be delivered to the nozzle through the dosing system separately or as a mixture with variable rates. Each of the components can go to any of the lines 12, 14, 15, 17. For example, the component from tank 5 can go to the transmission lines 12, 15 and the component from tank 6 goes to the transmission lines 14, 17. By switching pumps with valves 71, 72, 73, 74 one can direct either of the components into the mixers 81, 82, 83 or both components into the mixers. The valves can adjust the flow rate of the components going through the transmission lines, so different ratios of the two components can be obtained at the entrance of the mixers 81, 82, 83.

The temperature in the tanks 5, 6 and in the mixers 81, 82, 83 can be adjusted from room up to 90 degrees Celsius with a temperature step of 1 to 2 degrees.

Several pumps are used to avoid creation of vacuum/air bubbles/cavities inside the polymeric solutions and overload of the polymer entering into the tanks/mixers. They are synchronized and can be controlled by a computer program that calculates optimal flow rates of the pumps. The pumps are equipped with pressure sensors to control the flow rates and load.

Figure 7:
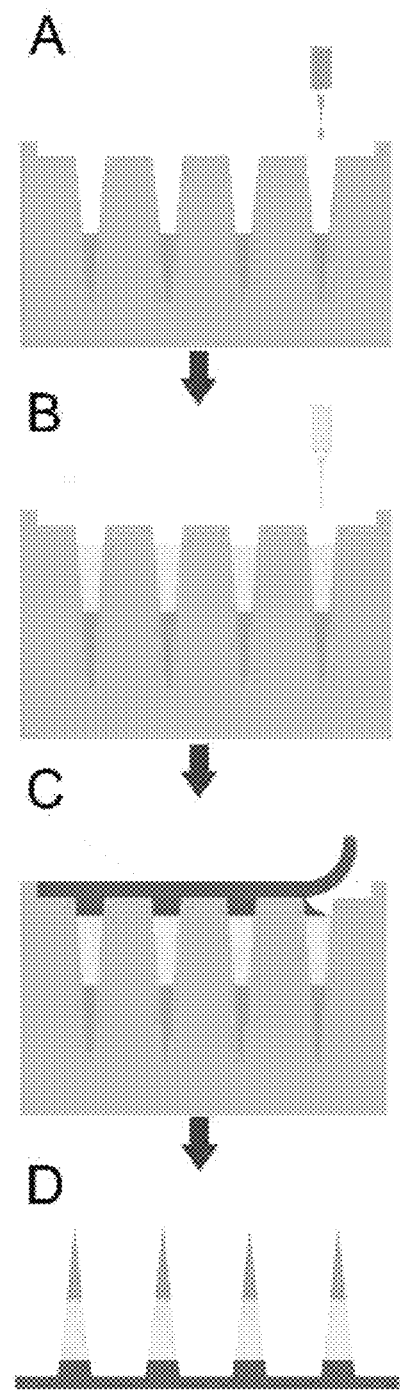
FIG. 7. A-D. Exemplary schemes of the process of fabricating 3-layer microneedles. A: Each microcavity of a PDMS microneedle mold was filled with drug-polymer solution under vacuum in the amount of 0.035 µl, after which it is dried. B: On top of the first layer with the dried drug-polymer solution, a second layer is dispensed with an "quick-dissolving" polymer (according to one embodiment it is carboxymethylcellulose) in this example an amount of 0.057 µl. C: The third layer of polymer solution is applied to the surface of the mold as a back layer and the layer is also dried. D: A backing coated with a thin film of concentrated polymer solution was placed on top of the mold and then air dried. After drying, the 3-layer microneedles were peeled off.

The fabrication process comprises three main stages of the production of microneedles shown in FIG. 7:

1. Precision insertion into each micro-cavity $1^{st}$ layer of drug-polymer composition, followed by vacuuming and drying;
2. Precision insertion into each micro-cavity of the 2nd layer. It can be a "quick-dissolving" polymer or a second drug-polymer solution, also followed by vacuuming and drying;
3. Preparation of the 3rd layers superficially on the mold as a back-layer and drying. The 3rd layer also partially goes into the base of the microneedles and forms a "pedestal", which does not contain any active components, but helps to introduce the needle tip with the active component beyond stratum corneum.

This method allows uniform drug loading into each microneedle without loss of the active substance and creates detachable dissolving microneedles (DDMN) due to the presence of a quick-dissolving layer between the tip of the "capsule" with the active substance and the back. Such microneedle drug delivery systems are relevant for substances requiring prolonged release from the capsule into the body (e.g. hormones, insulin). For this type of microneedle, there is no need to long-term wearing of the applicator on the skin and ensuring constant pressure on the microneedles with the help of various devices, since the intermediate layer between the back of the applicator and the needle tip dissolves, leaving a "capsule" with medicine or cosmetic agent in the skin.

Figures 5, 5A, 5B:
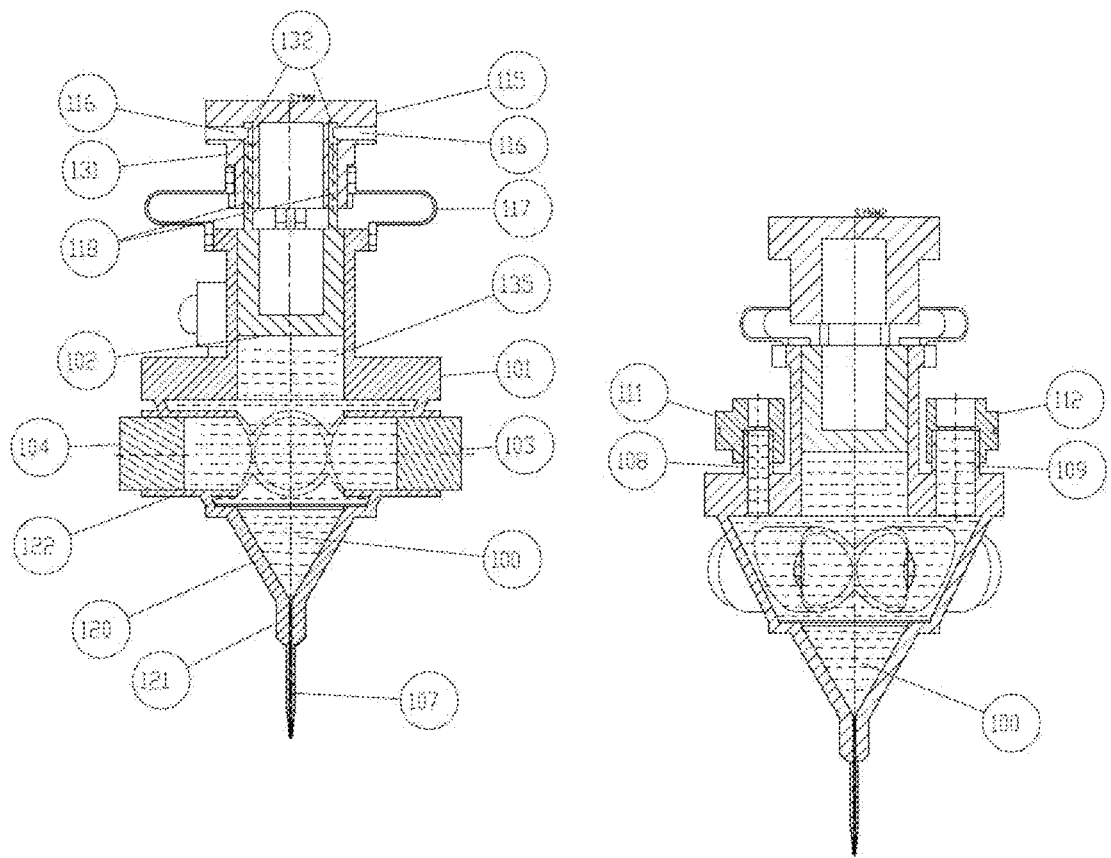
FIG. 5, composed of FIG. 5A
FIG. 5B shows vertical cross-sections of the adaptive injection device.
In FIG. 5A, a section going through the tubes 122 is shown.
Figure 6:
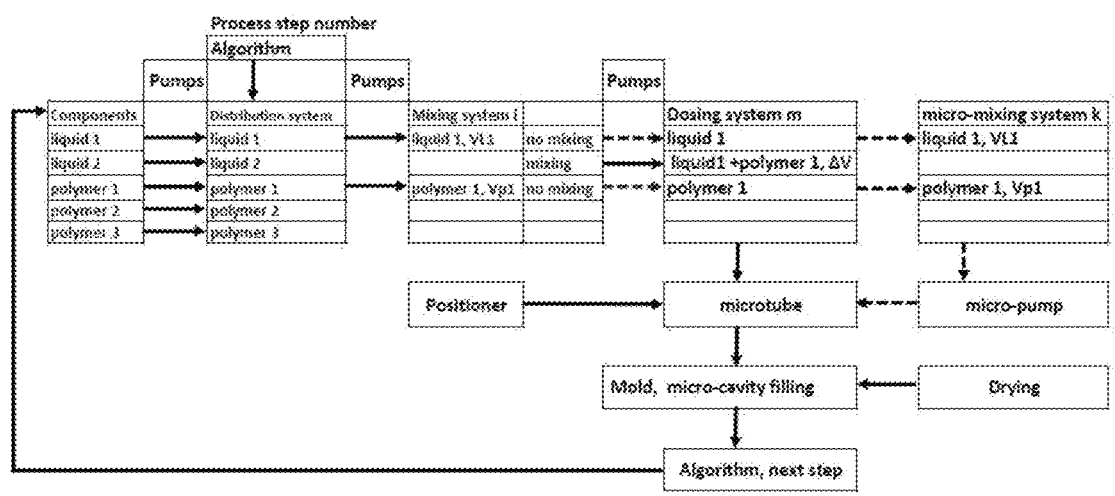
FIG. 6. A diagram of the fabrication process.

The injection nozzle shown in FIG. 4 and FIG. 5 comprises an injection head 101 having a cavity 100, at least two inlets 108, 109 for adding/removing materials into/from the cavity, valves 111, 112; a piston device 102 for adjustment of volume and pressure, one or more additional pistons 103, 104, 105 for fine movement, preferably, using piezoelectric crystals; a microtube 107 for injection of the liquid material into the microcavities of the mold 1 with optionally supplied ultrasonic vibrator 106. The frequency of the ultrasonic vibrator ranges from 1 KHz to 5 MHz and is correlated with viscosity of the liquid material. The upper piston is provided with springs 117, to adjust pressure of the plunger to the liquid component. The piston can move along the cylinder of the injection head. The movement is controlled by the upper flange 115 which is supplied with the holes for directing shafts 118 of the piston device 101. The pressing force onto the shafts of the piston can be established through pneumatic or hydrostatic pressure through holes 116. The inlets have different diameters, the bigger one 109 is used for adding base components and the smaller one 108 for active components.

When the liquid components are ready for use, they are transferred into the cavity 100 of the injection head. The upper control piston 102 adjusts the internal pressure. The injection pistons 103, 104, 105 are activated by applying an electrical pulse which causes step movement of the piton or/and deformation of the membrane. The control piston 102 moves inside the cavity compressing the liquid/polymeric solution inside the cavity until the working threshold pressure is reached. The inner pressure of the liquid is increased so that it enables to overcome capillary counter forces in the microtube 107 and a fraction of the liquid flows through the microtube following with dropping the liquid droplets into the microcavity of the mold. This results in the loss of the mass of the liquid component and decreasing the inner pressure. This results in returning the system into equilibrium. During this stage, the injection head is transferred to the next microcavity and the process is repeated until all microcavities of the mold are filled. The mass of the liquid droplet is controlled by the increase of the internal pressure and duration of the compression phase. This process can be controlled automatically, therefore the injection head is an adaptive one.

When two or more injection nozzles are used, then one can accelerate the injection process. The distances between the nozzles 120 are adjusted so that all the nozzles 120 fit with the microcavities and the filling the microcavities can be carried out simultaneously from all injection heads. After all microcavities are filled with the liquid components of the specific layer, they are dried in special conditions until the liquid transforms into a solid phase and the outer surfaces of the components are nuclearized and became stable. Then the next layer can be similarly fabricated on top of the previous one. Due to conic-like geometry of the micro-cavity and upward increasing diameter of the cavity, the next volume of the liquid component is increased. So, control parameters of the pumps, micropumps and injection heads are changed accordingly in accordance with the receipt.

In the disclosed design the fabrication device comprises two big tanks for the liquid components. In practice, more tanks can be connected to the system as well. In the figures there are two tanks 5, and 6, shown for simplicity.

One of the tanks 81, 82 and 83 (called mixers), a first stage mixer, of the dosing system is used to separately mixing two liquids keeping materials sterile, one of which is a blank/base liquid polymer compound without active components forming the first layer (sharp end) with the liquid fraction of medical or cosmetical component.

Other polymeric solutions forming the $2^{nd}$ and the $3^{rd}$ layers of the microneedle, as well as a blank/base polymeric solution of the $1^{st}$ layer, are prepared separately, not in the dosing system, as most of the soluble polymers require relatively high power for intensive mixing, heating etc. Moreover, at the beginning of the dissolution of the soluble polymers, large granules can be formed that can destroy small tubes and low-power mixer devices.

There are two key points related with polymeric solutions:
1. Generally, polymeric solutions are prepared in advanced before they go to the dosing devices.
2. Solution for the first layer is the mixture of a liquid highly concentrated medical or cosmetic component and a base polymer. According to one embodiment this solution may form the entire microneedle as well.

3. Mixing polymers 2 and 3 is carried out prior to entering the dosing system. The purpose is to add more functionality of the multilayer needle.

The invention is now described with non limiting examples.

Example 1: Microneedle Properties and Characterization

For the manufacture of 3-layer microneedles, thee different solutions were prepared for layer-by-layer pouring mold into the wells. The following chemical compositions and parameters were used as an example only. Other materials that meet the physical and chemical properties of the dissolution process can be used too.

For example, for the first layer (needle tip) an aqueous blend of 15% w/w Gantrez AN-139 (adjusted to pH 4), 7.5% w/w PEG 10,000 can be used. Hydrophilic fluorescent dye Rhodamine B (479 Da, Sigma, USA) can be used as model drug and as a coloring agent. Rhodamine B can be dissolved in deionized water to prepare stock solutions at concentration of 1 mg/mL. Rhodamine B and polymers can be dissolved in deionized water, homogenized and degassed simultaneously with a planetary centrifugal mixer (LMC-3000, BioSan, Latvia), and used as polymer solution. Layer of MN can be crosslinked (esterification reaction) by heating at 80° C. for 24 hours.

For the 2nd layer (middle of the needle) ultra-low viscosity carboxymethylcellulose (CMC, Cat No. 360384, Aldrich, USA) can be dissolved in deionized water. For staining this layer and subsequent visualization, a Fluorescein sodium salt (Sigma, USA) can be used which was previously added to water to dissolve the CMC at a concentration of 0.5 mg/ml. Water can be then evaporated off until the concentration of solute (e.g., CMC) is approximately 20 wt %, which resulted in a viscous hydrogel. CMC can be concentrated by heating at 60-70° C. at ambient pressure or vacuuming at −50 kPa at room temperature. Formulation and properties of the second compound are designed and verified in terms of meeting the following criteria: the ratio of the specific dissolution rates of the carrier bio-soluble agent and the biosoluble component varies from 1:200,000 to 1:950,000, respectively.

The microneedle base (3rd layer) matrix material can be formed of a polymer blend comprising polyvinylalcohol (PVA) (MW2000, ACROS Organics, Geel, Belgium) and polyvinylpyrrolidone (PVP) (BASF, K17, Aktiengesellschaft, Ludwigshafen, Germany) (ratio 3:1). In order to make a suitable polymer solution, for example 50 wt % polymer solution, 3 g PVA can be dispersed in 4 mL DI water and heated at 60° C. for 3 h. Then, 1 g PVP can be then added to the PVA solution and mixed thoroughly using a spatula. The polymer blend can be incubated at 37° C. in a sealed glass bottle overnight.

It is to be understood that the above is provided for purpose of an example only and not for limiting the scope of the invention.

Example 2: Loading Solutions into the Mold

Figure 10:
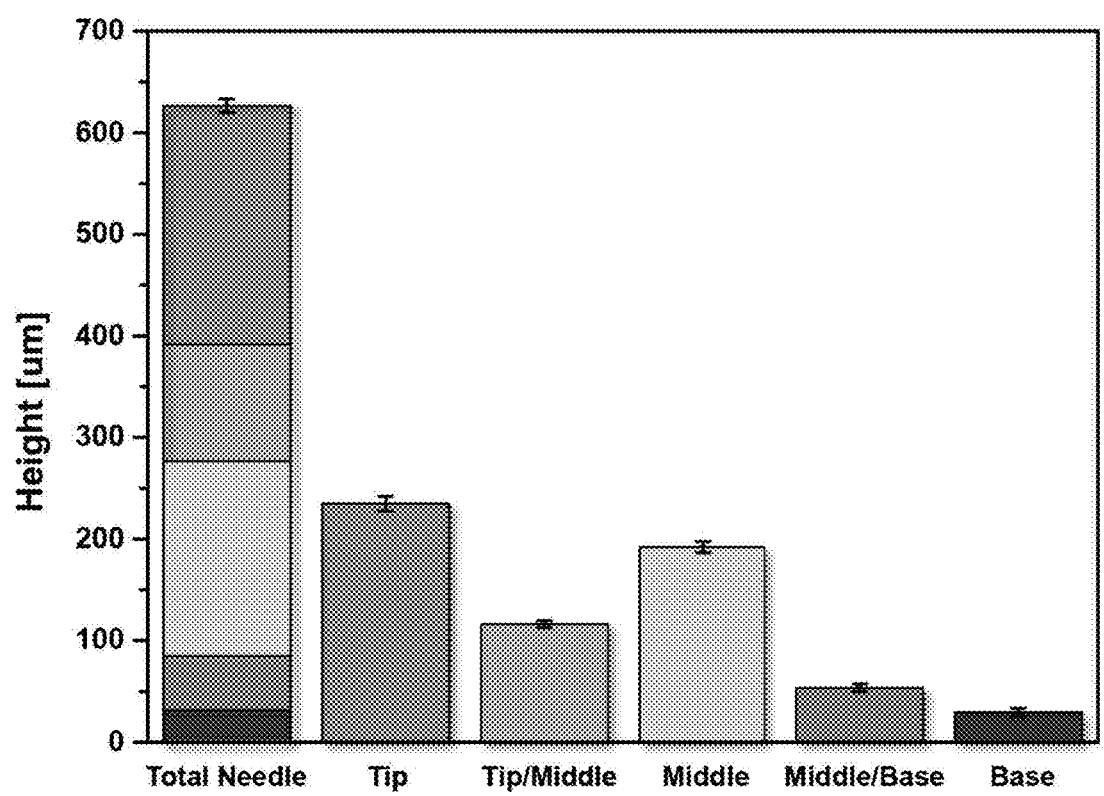
FIG. 10. Calculated mean and standard deviation of the height of the microneedles and each layer thereof.

Dosing of solutions directly into each well or microcavity of the mold is carried by using the device describe above. The positioning of the microtube 107 into each microcavity can be carried out using a positioning device with precision 3-axial positioning, for example, the X axis pitch ∼100 μm, the Y axis pitch ∼100 μm, and the Z axis pitch ∼20 μm. The first priming solution can be dosed into each micro-cavity for example in an amount of 0.035±0.01 µl, after which the solution is subjected to a drying and/or polymerization process. After that, the $2^{nd}$ solution is dosed into each micro-cavity in the amount of preferably 0.057±0.01 µl, followed by drying and/or polymerization. The third layer is poured evenly over the holes, forming the base of the microneedles. The ratio of the height of the section of conjugation of the layers (mixing) to the length of the entire needle is between 1: 600-1:300. According to one preferred embodiment the height of the first layer is between 30 and 50% preferably 45%, the height of the second layer is between 35 and 45%, preferably 40%, and the height of the base of the microneedles is between 10 and 20%, preferably 15% of the full length of the needle. FIG. 10 shows an example of the relations.

Example 3: Visual Assessment of Fabricated Microneedles

The quality assessment of the needles at the time of manufacturing was carried out as follows: The microneedle array was visualized and uniformity was evaluated using USB Microscope Micron Mobile Sititek 500× with the subsequent determination of the size of the microneedles in an array using PortableCapture software. Measurements of total MN length along with height of layers of the MNs were carried out using ImageJ software. To evaluate the mean and SD values of total MN length and height of the MN layers the measurements were accomplished using 10 random microscope fields of view. Results are shown in FIG. 10.

Figure 9:
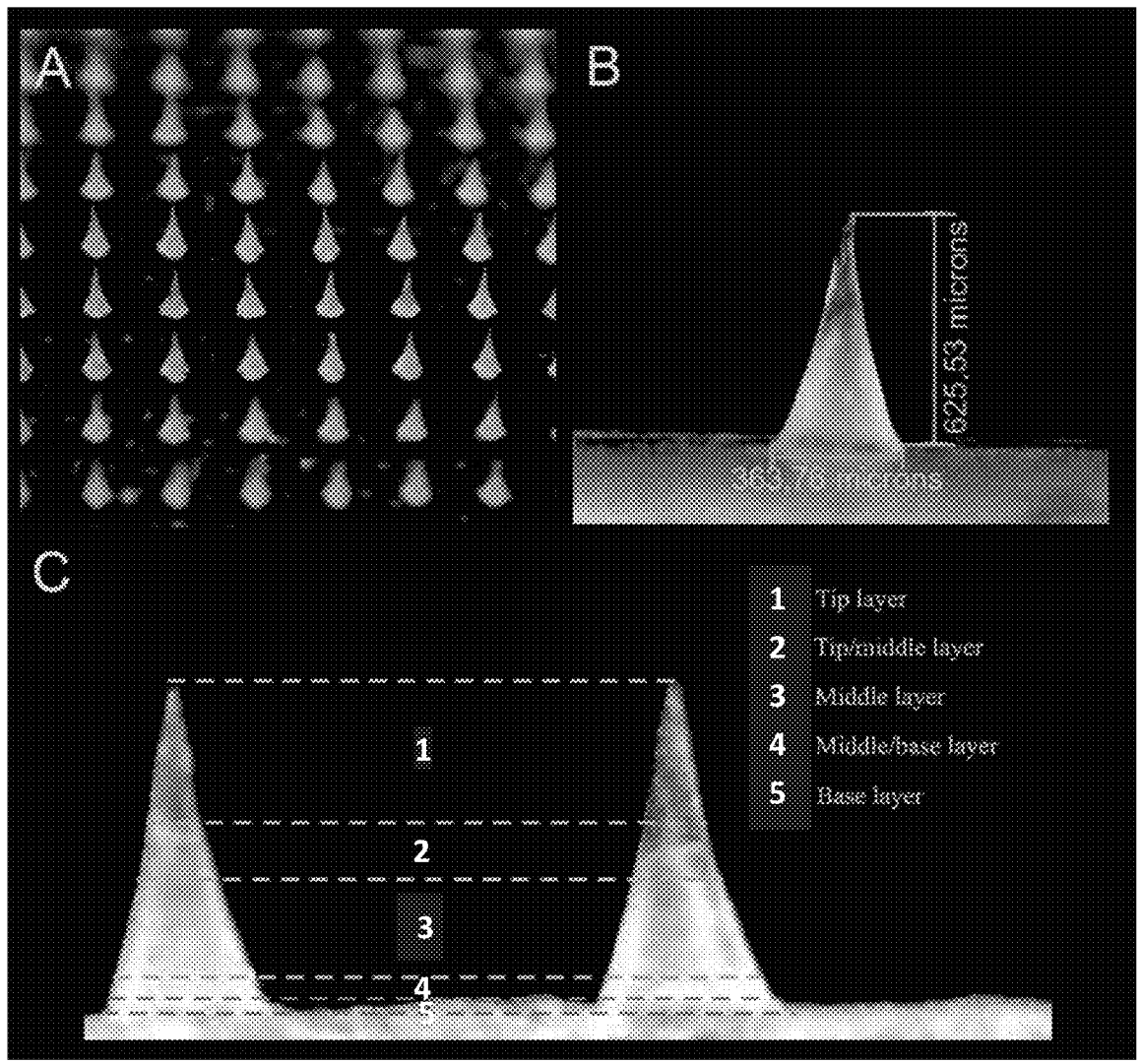
FIG. 9. A-C. The results of visual assessment of MN array. A) Uniformity of MN array; B) MN length and base diameter measurement; C) Measurement of the length (height) of MN layers.

A more precise determination of the dimensions of single microneedles from the array (i.e. MN size, shape and sharpness) were obtained by using EVOS FL Auto 2 Imaging System (Thermo Fisher Scientific, USA). FIG. 9 shows results of such determinations.

Example 4: Microneedle Mold

A mold is made of PDMS substrate and a matrix of micro-well structures is fabricated using a laser micromachining technique. The process is performed in one step. For example, a mold of a 10×10 array of 365 µm*365 µm*635 µm (W*L*H) conical microneedles with tip-to-tip spacing of 1000 mm was fabricated on a PDMS MN plate sample by drilling micro-wells with a laser. The sample, for example, was a 2-mm-thick PDMS sheet. The laser micromashing technique is described in [Wang, Q. L. et al. 2016, Materials Science and Engineering: C, 65, 135-142.].

A microneedle master structure made of polydimethylsiloxane (PDMS) can be prepared, for example, using the following procedure. To obtain a PDMS sheet with uniform thickness, the PDMS was mixed in a 1:1 v/v ratio of prepolymer to curing agent and degassed in a 800 Mb vacuum for half an hour, followed by curing into a customized mold with smooth surfaces curing at 60° C. for 5 h, and then resultant PDMS sheets were peeled off from the mold. Carbon dioxide laser engraving machine having power of 50 W to 70 W was employed to drill micro-structures on surface of PDMS sheets. The generated micro-cavities are obtained with the following laser parameters: the focus length of lens is 1.5 and the diameter of focal spot is 25 µm, laser power was fixed at 63%.

Example 5: Microneedle Fabrication

The original fabrication processes were introduced to better control drug encapsulation and to reduce the time of the procedure of delivering the drug to a body by disconnecting the part carrying the drug from the back of the patch. The method is based on precision layering of various compounds (polymers) directly into each micro-cavity of the casting mold, using the precision dosing device shown in FIG. 1. The dosing device includes a high-torque stepper motor controllers for precision positioning of the needles above the micro-cavities; syringe pump; ultrathin dispensing needles with an inner diameter of 50 microns; "machine vision" type sensors that additionally correct the positioning of the needle just above the micro-cavity and "lowering" the needle into at 200-300 microns.

The fabrication process involves 3 main stages of the production of microneedles shown in FIG. 7:
1. Precision insertion into each micro-cavity: The first layer of drug-polymer composition, followed by vacuuming and drying;
2. Precision insertion into each micro-cavity of the second layer. It can be a "quick-dissolving" polymer or a second drug-polymer solution, also followed by vacuuming and drying;
3. Deposition of the third layer superficially on the mold as a back-layer and drying. The third layer also partially goes into the base of the microneedles and forms a "pedestal", which does not contain any active components, but helps to introduce the tip with the active component beyond stratum corneum.

Figure 8:
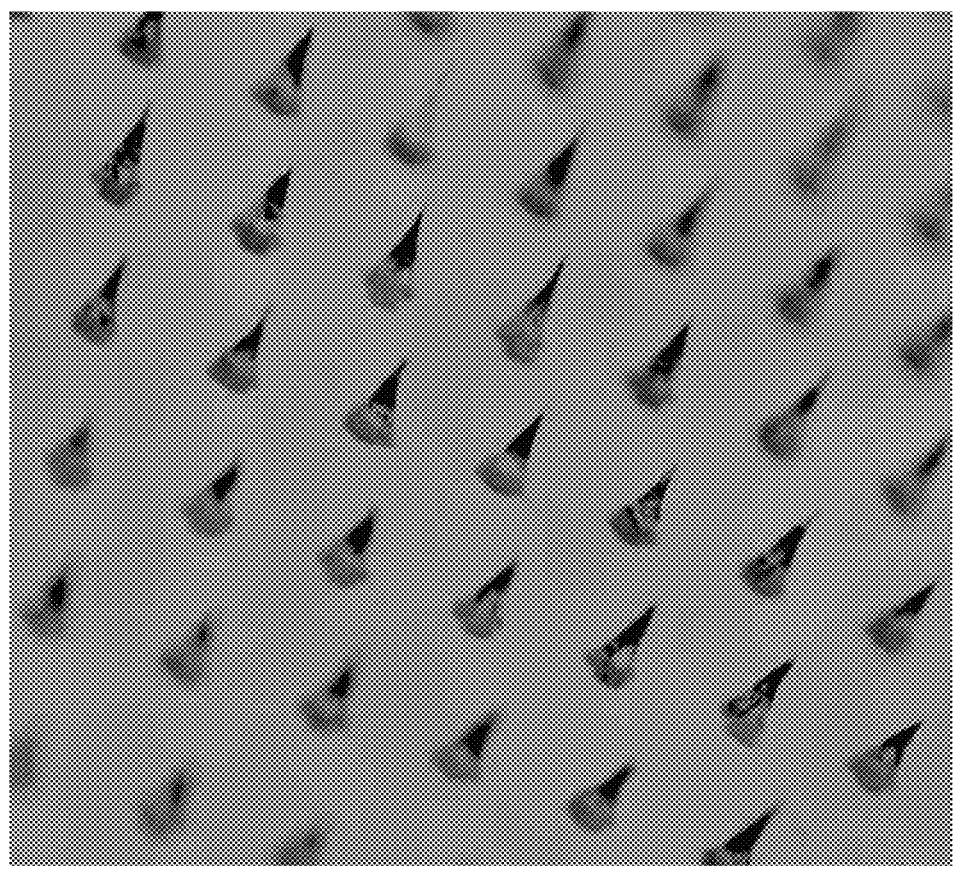
FIG. 8. shows a ready to use PDMS microneedle patch.

The procedure of 3-layer microneedles fabrication process may include, for example, the following materials.
A: Each cavity of a PDMS microneedle mold is filled with a drug-polymer solution under vacuum in the required amount. In this example the amount was 0.035 µl in one of the samples, after which it is dried.
B: On top of the first layer with the dried drug-polymer solution, a second layer is dispensed with an "quick-dissolving" polymer, for example, carboxymethylcellulose in an required amount. In this example the amount was 0.057 µl.
C: The third layer of polymer solution is applied to the surface of the mold as a back layer and also dried.
D: A backing coated with a thin film of concentrated polymer solution was placed on top of the mold and then air dried. After drying, the 3-layer microneedles were peeled off. FIG. 8 shows one of the fabricated microneedle patches.

This technology allows uniform drug loading into each microneedle without loss of the active substance and create detachable dissolving microneedles (DDMN) due to the presence of a quick dissolving layer between the tip of the "capsule" with the active substance and back. Such microneedle drug delivery systems are relevant for substances requiring prolonged release from the capsule into the body (e.g. hormones, insulin). For this type of microneedle, there is no need to long-term wearing of the applicator on the skin and ensuring constant pressure on the microneedles with the help of various devices, since the intermediate layer between the back and the needle tip dissolves, leaving a "capsule" with medicine in the skin.

For validation and verification of precision dosing technology to create microneedles, a set of test 3-layer microneedles with an average quick-dissolving layer of carboxymethylcellulose were manufactured as shown in FIG. 9. The main quantitative and qualitative parameters for these microneedles (dimensional characteristics, distribution of layers, failure force and etc.) were evaluated.

The structural analysis revealed that the shrinkage of dried polymer solutions occurring during fabrication process of 3-layered microneedles via "solution casting—drying"

per layer affects negligibly towards MN dimensions. The appearance of two intermediate layers localized between "tip layer/middle layer" and "middle layer/base layer" respectively (FIG. 9C) along with its small values of SD (FIG. 10) could be attributed to rhodamine B and uranine dye naturally occurring diffusion through interfaces of polymer layers. It can also be noted that when comparing the ratio of the heights of the layers in different microneedles in the array, low variability of values was established (no statistically significant differences, $p \geq 0.05$), which indicates the high reproducibility of the precision dosing method.

Example 6: Mechanical Strength and Microneedle Failure Analysis

Mechanical strength of the microneedles was studied based on failure analysis as it is described by Demir Y. K. et. al 2013. PLOS ONE 8(10): e77289. The force required for mechanical fracture of the microneedles was tested under axial compression load using micromechanical tester TA.XTplus Texture Analyser (Stable Micro Systems, UK) and an original cubic metallic mill (length, 3 cm; cross-sectional area, 2 mm$^2$) which was fixed on the upper station. A single MN was pressed into the metal mill that drove the microneedle against cubic metallic mill at a rate of 0.01 mm/s until a preset displacement of 500 mm was reached.

The mill and MN were aligned using a microscope camera. Upon maximum force application, the force either suddenly decreased or saturated. All needle failure forces are verified microscopically.

Figures 11, 12:
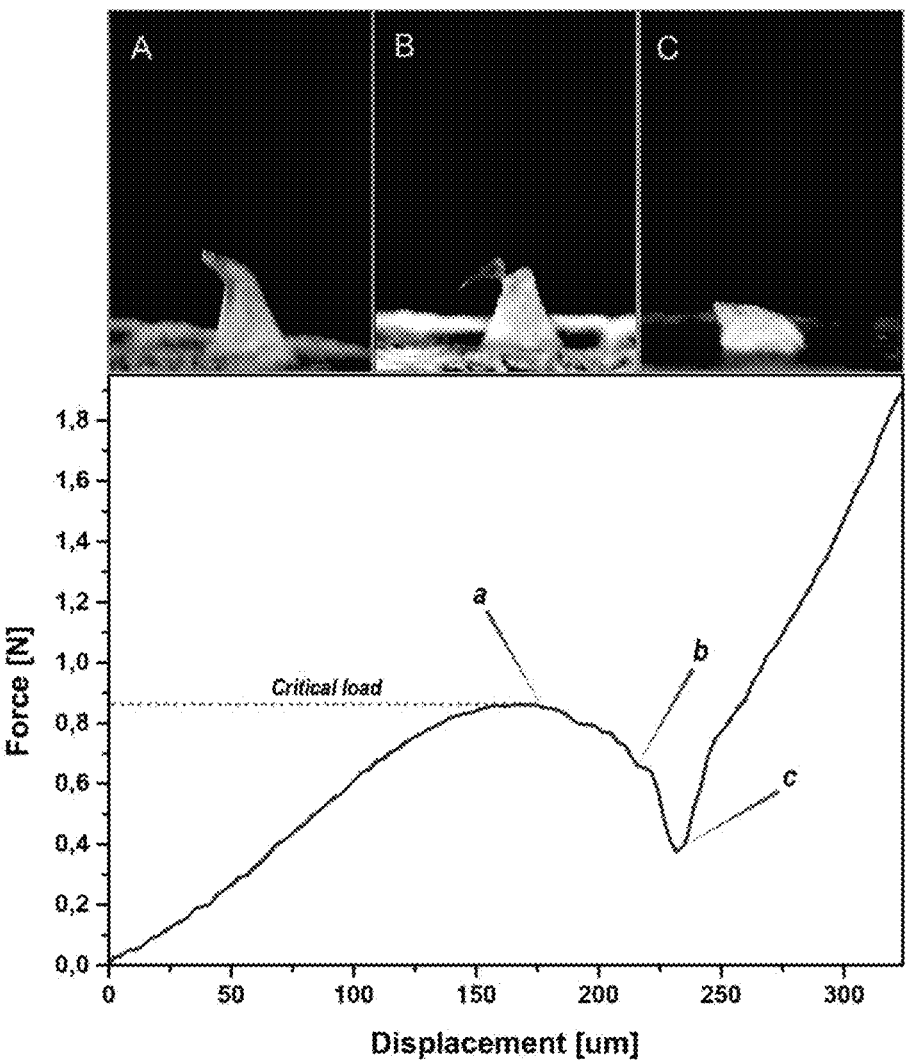
FIG. 11. Mechanical strength of a 3-layered detachable MN. Force is measured as a function of microneedle displacement while pressing against a rigid metal plate surface. The images of the microneedle of the MN failure test show the following features: a) critical load; b) fracture near tip layer; c) Squeeze of the remaining lower MN structures.
FIG. 12. 3-layer PDMS microneedles at the critical points a), b) and c) as shown in FIG. 11.

Results of measurements of incident forces, MN failure forces, that have caused MN failure are revealed in FIG. 11 and FIG. 12. The measurement of MN failure force revealed that the value of critical load of 3-layered detachable microneedles is around 0.87 N (FIG. 11 point "a") for the above MN example. The microscopic examination of MN after failure force test showed that the displacement of microneedles from 0 to approximately 170 µm cause microneedle tip bending up to ~50° exposing no visual signs of fracturing (FIG. 12A). Further MN displacement to over 200 µm led to MN fracture (FIG. 11 point "b") localized approximately at the center of MN middle layer composed of CMC (FIG. 12B). Finally, the even larger increase of MN displacement ended up having the fractured upper MN structures (i.e. tip and partially middle layer) unsettled from the main MN axis (FIG. 11 section between points "b" and "c") with further squeezing of MN remaining lower structures (i.e. microneedle base and partially remaining middle layer) (FIG. 11 point "c"; FIG. 12C).

In accordance with the revealed critical load value and general mode of MN failure we assume that during the MN displacement MN tip made of Gantez AN-139 (Young's modulus ~6.43 GPa) performs as a lever that displace the tension center downwards to centroid of middle layer made of CMC (Young's modulus about 1 GPa) where the fracturing starts. The current hypothesis seems to be consistent with previous studies.

Example 7: Force Plate Measurements

Parafilm1 M (PF) film was used as a skin simulant for MN insertion studies as described by Larrañeta et. al. 2015 Materials Science and Engineering: R: Reports, 104, 1-32.

Briefly, a sheet of Parafilm1 was folded to get an 8-layer film (1 mm thickness) and placed on a sheet of foamed poly(ethylene) for support. MN arrays were inserted using the station of the micromechanical tester TA.XTplus Texture Analyser (Stable Micro Systems, UK). Once the target force was reached, the probe was moved upwards at a speed of 0.5 mm/s. The MN arrays are removed from the polymeric sheet after insertion, then the penetrated PF sheet is unfolded and the number of holes in each layer is evaluated using a USB Microscope Micron Mobile Sititek 500×. In order to ease the detection of the created holes in the PF layers, the sample was placed between two polarizer filters. The thickness of each PF layer was determined as 126±7 µm and was used to calculate the percentage of MN inserted as a function of the depth.

Figure 13:
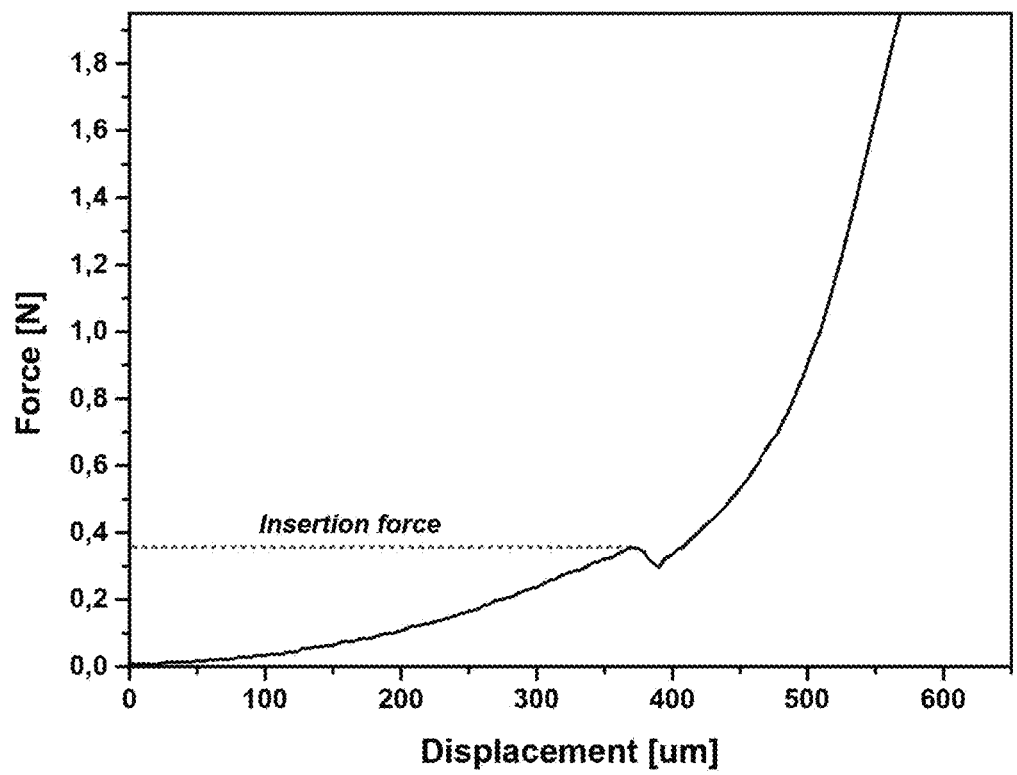
FIG. 13. 3-layered detachable dissolving microneedles (DDMNs) insertion force against Parafilm M1.

The analysis of the obtained curve describing MN insertion behavior allows for the conclusion that Parafilm M1 penetration by 3-layered detachable MN occurs at about 0.35N, thus, it could be assumed that the force needed for MN insertion is comparable with one needed for pressing the elevators button. The results of MN insertion force measurement against Parafilm M1 is shown at FIG. 13.

DDMNs showed 100% of skin insertion frequency. That means that all DDMNs penetrated and inserted into skin model without buckling or fracture of DDMN structure. Evaluation of the penetrated layers of Parafilm M1 showed that 100% of microneedles penetrated 4 layers (which corresponds to a depth of 510±7 micrometers) and about 2% reaches 5th layer.

Example 8: Live Detection of DDMN Separation in Agarose Gel

Agarose gel (2.0% w/v, molecular biology grade, Invitrogen, France) was used for live imaging of MN-separation from the pillar array. Fabricated DDMNs carrying methylene blue dye (further methylene blue was substituted by black iron oxide pigment solution) were penetrated into the agarose gel and removed after 5, 10, 15, 20, 25, and 30 s of exposure. DDMN-separation images were taken simultaneously with a microscope (Micron Mobile Sititek 500×, Korea). All tests were repeated four times under the same conditions. The tests have been performed in accordance with Kim M et al. [PLoS One. 2015 Aug. 26; 10(8): e0136513].

Figure 15:
FIG. 15. Agarose gel sample pierced by tested DDMN (perpendicular slice).

The main task of this test was to determine the behavior of 3-layer microneedles in contact with liquid, estimated the time required to dissolve the $2^{nd}$ quick-dissolving polymer and separate the tips of microneedles in the entire microneedle array. FIG. 15 shows a cross section of an agarose gel after penetration of the microneedles.

Figure 14:
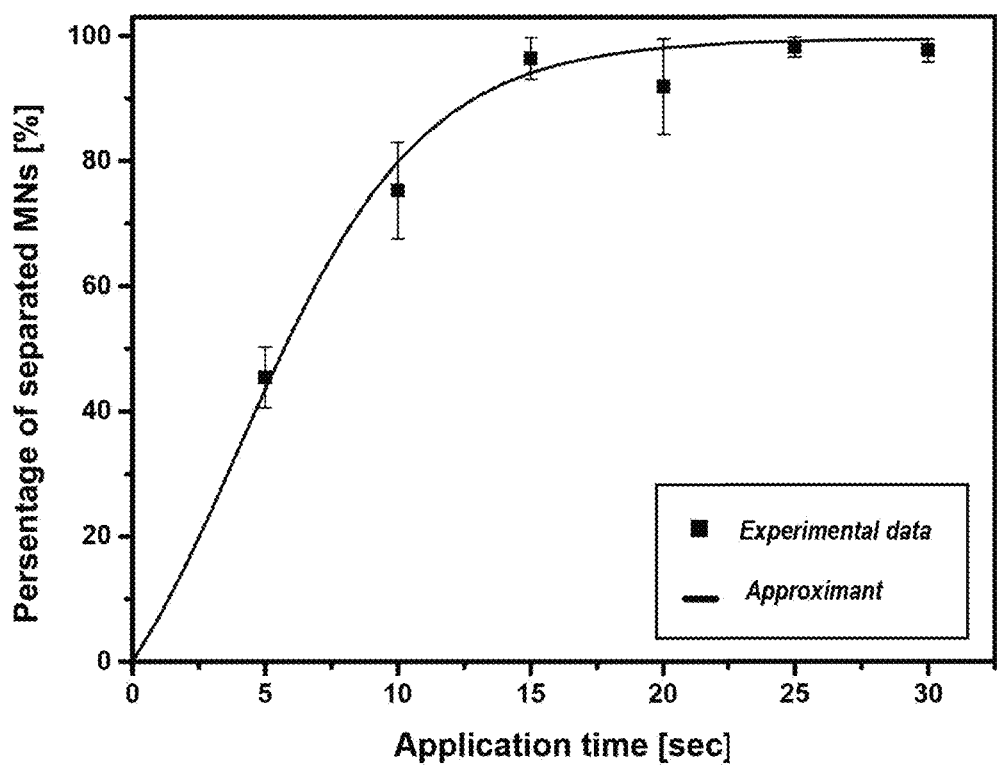
FIG. 14. Measured percentage of separated DDMNs after insertion in agarose gel.

The results of measurement of percentage detachable microneedles layers separation in agarose gel versus insertion time are shown in FIG. 14.

The behavior of approximation function suggests that over 98% of DDMN separate from base layer after microneedles insertion in agarose gel for 25 seconds.

The images of agarose gel slices made after 10, 30 and 60 seconds after DDMN insertion (FIG. 15, FIG. 16) show the rapid dissolution of MN middle layer made of CMC. At the same time, MN tip layer structure, in contrary, remained much less affected by agarose gel moisture after 60 seconds of insertion. The obtained results indicate the ability of DDMN to form sustainable drug release sites within high water content model media imitating human skin.

FIG. 16 (A,B) displays microphotographs of slices of agarose gel punctured by Type 1 DDMN. According to agarose gel pattern of DDMN punctures, despite the obvious fact of DDMN tips detachment occurring within agarose gel puncture sites, the tested microneedles tend to rapidly lose their structural and geometrical integrity due to much higher water content within agarose gel in comparison with residual moisture content within cadaver skin samples. The aforementioned fact, thus, handicaps are detected at DDMN separation.

Aiming to overcome the previously described handicap and increase test reliability, drug load imitating solution occurring within microneedle tips of Type 1 DDMN was changed form 1% aqueous solution of methylene blue dye to 0.05% w/w aqueous solution of black iron oxide pigment. The images exhibiting results of reiterated test considering live detection of DDMN separation within agarose gel are given at FIG. 16. According to the presented images, microneedles of tested DDMN sample readily detach from DDMN path back (FIG. 16 A,B).

It is worth noting that tips of DDMN captured at images presented at FIG. 16 exhibit detachment behavior comparable to one uncovered in case of testing Type 1 DDMN. The foregoing results suggest that DDMN tips tend to detach once DDMN are inserted into bulk moisture media regardless to the properties of drug loaded into DDMN tips. However, structural and geometrical behavior of detached DDMN tips within puncture site remains unclear in terms of how does moisture rich media affects DDMN tips having different composition and length.

Example 9: Microneedle Insertion into Skin

Excised hairless human cadaver skin and porcine cadaver skin was used to assess the efficiency of penetration of microneedles. The human cadaver skin was collected and stored according to the approved Perm State Medical University named after Academician E. A. Wagner IRB/REC guidelines. The skin's subcutaneous fat was removed by a scalpel (Vorsma, Russia). The processed skin was laid flat on a cutting board at room temperature. The surface of the skin was wiped with 70% isopropylalcohol wipe, then wipe clean with a paper towel. Microneedles: a) carrying no dye within tips (Type 0), b) carrying methylene blue dye (Type 1) were manually inserted into the skin while positioning two fingers on either side of the intended insertion site to keep it under mild tension. DDMNs were manually inserted into the skin for 20 min with further removal of DDMN patch.

In case of testing Type 0 DDMNs, pierced human (or porcine) cadaver skin was treated with dye solution by applying 1% methylene blue solution, the solution was applied for 1 min on the skin. After a 1-minute exposure to the dye, the skin was washed with distilled water to remove the dye around the punched parts. Penetrated skin (both Type 0 and Type 1) was visualized using USB Microscope Micron Mobile Sititek 500× (SITITEK, Hong Kong). Each subset of microneedles for each insertion time had 3 replicates. Results are shown in FIGS. 17-20.

Human Cadaver Skin:

The patterns of puncture occurred after DDMN insertion into human cadaver skin sample are depicted at FIG. 17. The foregoing images clearly indicate the fact of DDMNs successful human cadaver skin penetration after microneedle application using the force not exceeding previously determined value (about 0.35 N).

Porcine Cadaver Skin:

The appearance of Type 0 DDMN before and after insertion test along with porcine cadaver skin surface pattern before and after insertion test is depicted at FIG. 18. The captured images show DDMN pronounced porcine skin piercing and detachment capabilities when DDMN are applied using force approximately equal to the foregoing value (about 0.35 N) and stated DDMN testing exposure time (20 min).

The images presented at FIG. 19 also display comparable pattern porcine cadaver skin morphology alteration after DDMN application:

The analogous results were obtained for Type 1 DDMN when tested at the same experimental conditions (FIG. 20). The analysis of the images presented at FIG. 20 suggests that DDMN skin piercing followed by detachment of MN tips carrying dye solution successfully occurred in accordance with DDMN expected specifications.

The obtained data analysis results allow for the conclusion that under similar experimental conditions imitating DDMN devise usage by regular consumer the designed microneedles show repeatable tendency of consequent skin piercing followed by MN tips detaching within skin puncture sites irrespective to loaded drug properties.

LIST OF ELEMENTS

1—mold
2—base
3—horizontal sliding mechanism in x-direction
4—slider z-direction
5, 6—tanks of liquid/polymeric material
7—distribution device
10,11—transmission lines 12, 14, 15, 17—tubes
19 a-d, 20a-d—transmission lines
21—rods
22—rods
25—rods
23—slider x-direction
25—rods
27—horizontal sliding mechanism y direction
28—slider y-direction
31—vertical sliding mechanism z-direction
43—motor y-direction
44—motor z-direction
41—motor x-direction
71,72, 73, 74—pumps with valves
75, 76—pumps with valves
81,82, 83—mixers
91, 92, 93, 94—mixers with pumps
100—cavity
101—flange
102—piston
103, 104,105—pistons
106—vibration device
107—microtube
108, 109—inlets 108 smaller/109 larger
110—end of the microtube
111—pump with valve
112—pump with valve
115—flange
117—fixation springs
120—injection nozzle
121—vibrator
122—tubes
131—pressing mechanism with force control
135—hole

What is claimed is:

1. An apparatus for manufacturing a multilayer microneedle patch, comprising:
a mold having a plurality of microcavities;
one or more containers for holding at least one liquid chemical material and active components;

an injection assembly connected with the one or more containers, the injection assembly comprising at least one adaptive injection device comprising a nozzle having an inner cavity, and at least two inlets to fill the inner cavity with the at least one liquid chemical material, a piston for adjustment of volume and pressure in the inner cavity, and a microtube for injection of the at least one liquid chemical material to the plurality of microcavities; and a positioning mechanism comprising horizontal and vertical sliding rods configured to provide a precise movement of the injection assembly along three perpendicular axes above the mold;

wherein at least one mixer is combined into a first stage mixer and is connected to a transmission line connecting a dosing system comprising a multitude of mixers with the one or more containers thereby enabling preparation of base polymeric components before transferring the components with controlled volume to the injection assembly.

2. The apparatus of claim 1, wherein the plurality of the microcavities of the mold have conical shape, and the mold is oriented in a horizontal plane, and the nozzle of the injection assembly is oriented perpendicularly to an upper surface of the mold facing the plurality of microcavities.

3. The apparatus of claim 2, wherein the dosing system is configured to prepare liquid chemical materials composed of polymers to polymeric solutions for a multilayer structure of tho microneedles.

4. The apparatus of claim 1, wherein the injection assembly comprises at least one additional piston for adjustment of volume of polymeric solution in the inner cavity and the microtube of the at least one adaptive injection device has an inner diameter small enough to create capillary forces of the polymeric solution inside the microtube to resist polymer flow through the microtube and prevent flow when an internal pressure of the polymeric solution inside the inner cavity is less than a specific flow pressure.

5. The apparatus of claim 4, wherein the at least one additional piston provides fast compression of the polymeric solution inside the inner cavity increasing the internal pressure of the polymeric solution inside the inner cavity to above the specific flow pressure within 1 to 500 ms, enabling injection of the polymeric solution from the inner cavity through the microtube into the plurality of microcavities of the mold, wherein a volume of an injected droplet of the polymeric solution is defined by difference between a first force and a second force, the first force being defined by pressure of the polymeric solution inside the inner cavity multiplied by a cross-sectional area of the microtube, and the second force being integrated force determined by the capillary forces inside the microtube, wherein the first and the second forces are opposite forces providing self-switching off injection process when the first force and the second force compensate each other.

6. The apparatus of claim 5, wherein the microtube is supplied with an ultrasonic vibrator that enables micro-vibrations of the microtube of the nozzle reducing the capillary forces.

7. The apparatus of claim 6, wherein a frequency of the ultrasonic vibrator ranges from 1 KHz to 5 MHz, and is correlated with viscosity of the polymeric solution.

8. The apparatus of claim 5, wherein the nozzle is supplied with an ultrasonic vibrator enabling micro-vibrations of the polymeric solution inside the inner cavity to make the polymeric solution more homogenous and improving flow of the polymeric solution through the nozzle.

9. The apparatus of claim 4 wherein the at least one additional piston for volume regulation is connected to an external pressing mechanism that provides an external force to the piston for compensation of the internal pressure of the polymeric solution in the inner cavity acting on an inner surface of the piston.

10. A method of manufacturing multilayer soluble microneedles and packaging the microneedles into a flexible patch for further use for transdermal injections of active bio-chemicals into skin comprising:
a) providing a mold having a plurality of conical microcavities;
b) preparing sequentially at least three different polymeric solutions for forming multilayers of microneedles;
c) by using the apparatus of claim 1, filling the conical microcavities with the polymeric solutions starting from a tip of microneedle structure, followed by deposition of at least one intermediate/middle layer, followed by deposition of at least one base layer;
d) vacuuming and drying each layer after the deposition;
e) depositing a superficial cover base layer forming a top patch structure by covering a top surface of the mold with a film providing strong mechanical connection of all microneedles to the cover base layer and formation of a flexible patch;
f) vacuuming and drying the cover base layer;
g) preparing adhesive and protection layers on top of the cover base layer; and
h) removing of the flexible patch from the mold.

11. The method of claim 10, wherein a first polymeric solution for a first layer forming a tip of a microneedle is prepared to comprise a hard polymeric solution with active components, and a second polymeric solution for a second intermediate layer is prepared to comprise a soluble polymeric solution that dissolves faster in skin than the first polymeric solution.

12. The method of claim 10, wherein the cover base layer is manufactured to contain another active component for treatment of top surface of skin.

13. The method of claim 11, wherein the first polymeric solution forming the first layer is prepared to include a drug-polymer composition, the second polymeric solution forming the second layer is prepared to consist of a quick-dissolving polymer, and a third polymeric solution forming a third layer is manufactured to form a back-layer and also configured to partially penetrate into the plurality of microcavities of the mold to form pedestals-like structures of the microneedles.

14. The method of claim 10, wherein additional functional layers are formed in between two neighboring structural layers by inter-diffusion of chemical components into a depletion layer at an interface between deposited layers.

* * * * *